(12) United States Patent
Tal et al.

(10) Patent No.: US 11,419,610 B2
(45) Date of Patent: Aug. 23, 2022

(54) DEVICE AND METHOD FOR PASSING TENSION MEMBER AROUND TISSUE MASS

(71) Applicant: Empress Medical, Inc., Wilmington, DE (US)

(72) Inventors: Michael Gabriel Tal, Tel Aviv (IL); Gilad Magnazi, Hod Hasharon (IL)

(73) Assignee: Empress Medical, Inc., Wilmington, DE (US)

( * ) Notice: Subject to any disclaimer, the term of this patent is extended or adjusted under 35 U.S.C. 154(b) by 200 days.

(21) Appl. No.: 16/752,934

(22) Filed: Jan. 27, 2020

(65) Prior Publication Data

US 2020/0155160 A1 May 21, 2020

Related U.S. Application Data

(63) Continuation-in-part of application No. PCT/US2019/064030, filed on Dec. 2, 2019, which is
(Continued)

(51) Int. Cl.
*A61B 17/12* (2006.01)
*A61B 17/42* (2006.01)
*A61B 17/04* (2006.01)

(52) U.S. Cl.
CPC .... *A61B 17/12013* (2013.01); *A61B 17/0485* (2013.01); *A61B 2017/12018* (2013.01); *A61B 2017/4216* (2013.01)

(58) Field of Classification Search
CPC ........ A61B 2017/4216; A61B 17/0485; A61B 2017/06052; A61B 2017/00367; A61B 17/062
(Continued)

(56) References Cited

U.S. PATENT DOCUMENTS 5,083,570 A 1/1992 Mosby
5,116,340 A 5/1992 Songer et al.
(Continued)

FOREIGN PATENT DOCUMENTS

CA 2634284 A1 * 7/2007 ......... A61B 17/0482
CN 203763237 U 8/2014
(Continued)

OTHER PUBLICATIONS

International Search Report and Written Opinion dated Oct. 7, 2019 in International Patent Application No. PCT/US2019/046384.
(Continued)

*Primary Examiner* — Katherine H Schwiker
*Assistant Examiner* — Serenity A Miller
(74) *Attorney, Agent, or Firm* — Veros Legal Solutions, LLP

(57) ABSTRACT

Disclosed are an apparatus and method for forming a passage extending along a plane crossing an organ's volumetric region from an entry point to an opposing exit point at a surface of the organ, and for passing a tension member around the volumetric region by pulling the tension member from the exit point to the entry point through the passage. The apparatus can include a rigid outer tube with a tip for penetrating the organ and reach a penetration depth; an inner needle with an elastic body configured to pass straightened through the outer tube lumen and to partially protrude and voluntarily flex to a curved form greater than the diameter of the volumetric region; and a tension member passer with a pulling portion for engaging with a portion of the tension member and for pulling the tension member when withdrawn.

24 Claims, 14 Drawing Sheets

Related U.S. Application Data a continuation-in-part of application No. 16/539,800, filed on Aug. 13, 2019.

(60) Provisional application No. 62/719,177, filed on Aug. 17, 2018, provisional application No. 62/774,249, filed on Dec. 2, 2018.

(58) Field of Classification Search
USPC .................................................. 606/141
See application file for complete search history.

(56) References Cited

U.S. PATENT DOCUMENTS

| | | | |
|---|---|---|---|
| 5,281,238 A | 1/1994 | Chin et al. |
| 5,417,700 A | 5/1995 | Egan |
| 5,439,467 A | 8/1995 | Benderev et al. |
| 5,447,512 A | 9/1995 | Wilson et al. |
| 5,484,399 A | 1/1996 | DiResta et al. |
| 5,611,357 A | 3/1997 | Suval |
| 5,735,289 A | 4/1998 | Pfeffer et al. |
| 5,788,709 A | 8/1998 | Riek et al. |
| 5,792,151 A | 8/1998 | Heck et al. |
| 5,846,180 A * | 12/1998 | Kulisz ............... A61F 2/0009 |
| | | | 600/29 |
| 5,957,936 A | 9/1999 | Yoon et al. |
| 6,102,920 A | 8/2000 | Sullivan et al. |
| 6,159,234 A | 12/2000 | Bonutti et al. |
| 6,254,601 B1 | 7/2001 | Burbank et al. |
| 6,471,715 B1 | 10/2002 | Weiss |
| 6,546,933 B1 | 4/2003 | Yoon |
| 6,550,482 B1 | 4/2003 | Burbank et al. |
| 6,602,251 B2 | 8/2003 | Burbank et al. |
| 6,605,097 B1 | 8/2003 | Lehe et al. |
| 6,659,105 B2 | 12/2003 | Burbank et al. |
| 6,764,488 B1 | 7/2004 | Burbank et al. |
| 6,905,506 B2 | 6/2005 | Burbank et al. |
| 6,936,048 B2 | 8/2005 | Hurst |
| 7,122,011 B2 | 10/2006 | Clifford et al. |
| 7,207,996 B2 | 4/2007 | Burbank et al. |
| 7,223,279 B2 | 5/2007 | Burbank et al. |
| 7,229,465 B2 | 6/2007 | Burbank et al. |
| 7,338,502 B2 | 3/2008 | Rosenblatt |
| 7,354,444 B2 | 4/2008 | Burbank et al. |
| 7,594,890 B2 | 9/2009 | Burbank et al. |
| 7,662,128 B2 | 2/2010 | Salcudean et al. |
| 7,771,357 B2 | 8/2010 | Burbank et al. |
| 7,842,050 B2 | 11/2010 | Diduch et al. |
| 7,875,036 B2 | 1/2011 | Burbank et al. |
| 7,883,475 B2 | 2/2011 | Dupont et al. |
| 8,137,372 B2 | 3/2012 | Kondoh et al. |
| 8,298,145 B2 | 10/2012 | Deckman et al. |
| 8,357,176 B2 | 1/2013 | Gross |
| 8,361,093 B2 | 1/2013 | Wright |
| 8,460,322 B2 | 6/2013 | Burg et al. |
| 8,528,563 B2 | 9/2013 | Gruber |
| 8,535,336 B2 | 9/2013 | Trovato |
| 8,568,385 B2 | 10/2013 | McIntyre |
| 8,574,253 B2 | 11/2013 | Gruber et al. |
| 8,647,367 B2 | 2/2014 | Kassab et al. |
| 8,795,295 B2 | 8/2014 | Sauer |
| 8,808,313 B2 | 8/2014 | Thorne et al. |
| 8,858,528 B2 | 10/2014 | Sicvol |
| 8,951,274 B2 | 2/2015 | Adams et al. |
| 9,095,366 B2 | 8/2015 | Sullivan et al. |
| 9,144,428 B2 | 9/2015 | Binmoeller et al. |
| 9,174,020 B2 | 11/2015 | Allen et al. |
| 9,198,664 B2 | 12/2015 | Fung et al. |
| 9,282,988 B2 | 3/2016 | Goshayeshgar |
| 9,289,205 B2 | 3/2016 | Rohl et al. |
| 9,301,770 B2 | 4/2016 | Gruber |
| 9,339,288 B2 | 5/2016 | Sullivan et al. |
| 9,392,935 B2 | 7/2016 | Adams et al. |
| 9,539,019 B2 | 1/2017 | Sullivan et al. |
| 9,808,237 B2 | 11/2017 | Murray et al. |
| 9,808,240 B2 * | 11/2017 | Parsons ............... A61B 17/0485 |
| 9,820,794 B2 | 11/2017 | Ott et al. |
| 9,936,956 B2 | 4/2018 | Fung et al. |
| 10,085,763 B2 | 10/2018 | Binmoeller et al. |
| 10,085,764 B2 | 10/2018 | Binmoeller et al. |
| 10,130,389 B2 | 11/2018 | Sullivan et al. |
| 10,143,475 B2 | 12/2018 | Ibrahim et al. |
| 2001/0047152 A1 | 11/2001 | DiResta et al. |
| 2002/0087178 A1 | 7/2002 | Nobles et al. |
| 2002/0124853 A1 | 9/2002 | Burbank et al. |
| 2002/0147456 A1 | 10/2002 | Diduch et al. |
| 2004/0010273 A1 | 1/2004 | Diduch et al. |
| 2004/0097962 A1 | 5/2004 | Burbank et al. |
| 2004/0127915 A1 | 7/2004 | Fleenor et al. |
| 2004/0202694 A1 | 10/2004 | Burbank et al. |
| 2005/0182433 A1 | 8/2005 | Nady |
| 2005/0245947 A1 | 11/2005 | Harmanli |
| 2006/0178698 A1 | 8/2006 | McIntyre et al. |
| 2006/0265042 A1 | 11/2006 | Catanese et al. |
| 2006/0276808 A1 | 12/2006 | Arnal et al. |
| 2006/0276871 A1 | 12/2006 | Lamson et al. |
| 2006/0287658 A1 | 12/2006 | Mujwid et al. |
| 2007/0038229 A1 | 2/2007 | Torre et al. |
| 2007/0225702 A1 | 9/2007 | Kaouk |
| 2008/0114382 A1 | 5/2008 | Mujwid et al. |
| 2008/0200939 A1 | 8/2008 | MacLean et al. |
| 2009/0043295 A1 | 2/2009 | Arnal et al. |
| 2009/0054916 A1 | 2/2009 | Meier et al. |
| 2009/0062599 A1 | 3/2009 | Brizzolara |
| 2009/0149808 A1* | 6/2009 | Hansen ............... A61M 25/1036 |
| | | | 604/103.04 |
| 2009/0222025 A1 | 9/2009 | Catanese et al. |
| 2010/0198235 A1 | 8/2010 | Pierce et al. |
| 2011/0071551 A1 | 3/2011 | Singhatat et al. |
| 2011/0093009 A1 | 4/2011 | Fox |
| 2011/0106107 A1 | 5/2011 | Binmoeller et al. |
| 2011/0166514 A1 | 7/2011 | Trovato et al. |
| 2011/0224596 A1 | 9/2011 | Flaherty et al. |
| 2011/0251455 A1 | 10/2011 | Popovic |
| 2011/0256225 A1 | 10/2011 | Ghoroghchian et al. |
| 2011/0295199 A1 | 12/2011 | Popovic et al. |
| 2012/0093716 A1 | 4/2012 | Jennische et al. |
| 2012/0123448 A1 | 5/2012 | Flom et al. |
| 2012/0271230 A1 | 10/2012 | Arnal et al. |
| 2013/0018385 A1* | 1/2013 | Keene ............... A61B 17/32056 |
| | | | 606/113 |
| 2013/0090526 A1 | 4/2013 | Suzuki et al. |
| 2013/0158578 A1 | 6/2013 | Ghodke et al. |
| 2013/0184680 A1 | 7/2013 | Brewer et al. |
| 2013/0324986 A1 | 12/2013 | Ott et al. |
| 2014/0271612 A1 | 9/2014 | Leppert et al. |
| 2014/0276913 A1 | 9/2014 | Tah et al. |
| 2014/0276979 A1 | 9/2014 | Sauer et al. |
| 2014/0276981 A1 | 9/2014 | Hendricksen et al. |
| 2014/0364835 A1 | 12/2014 | Allen et al. |
| 2014/0378963 A1 | 12/2014 | Batchelor et al. |
| 2015/0094739 A1 | 4/2015 | Norton et al. |
| 2015/0250476 A1 | 9/2015 | Feezor et al. |
| 2016/0120549 A1 | 5/2016 | Fung et al. |
| 2016/0120647 A1 | 5/2016 | Rogers et al. |
| 2016/0278781 A1 | 9/2016 | Fung et al. |
| 2016/0296244 A1 | 10/2016 | Thomas et al. |
| 2016/0346000 A1 | 12/2016 | Abreu |
| 2016/0348769 A1 | 12/2016 | Siegal |
| 2017/0007259 A1 | 1/2017 | Kimura et al. |
| 2017/0119455 A1 | 5/2017 | Johnson et al. |
| 2017/0128062 A1 | 5/2017 | Eguchi et al. |
| 2017/0360706 A1 | 12/2017 | Ghoroghchian |
| 2018/0008250 A1 | 1/2018 | Joseph |
| 2018/0028178 A1 | 2/2018 | Murray et al. |
| 2018/0228486 A1 | 8/2018 | Ravikumar et al. |
| 2018/0310941 A1 | 11/2018 | Fung et al. |
| 2018/0344312 A9 | 12/2018 | Diduch et al. |

(56) References Cited

U.S. PATENT DOCUMENTS

| | | | |
|---|---|---|---|
| 2019/0000497 A1 | 1/2019 | Binmoeller et al. | |
| 2019/0117229 A1 | 4/2019 | Ibrahim et al. | |

FOREIGN PATENT DOCUMENTS

| | | | |
|---|---|---|---|
| DE | 4317328 C2 | 8/1996 | |
| EP | 0669101 A1 | 8/1995 | |
| EP | 1967146 A2 | 9/2008 | |
| WO | 03034926 A1 | 5/2003 | |
| WO | 2006137051 A1 | 12/2006 | |
| WO | 2016007973 A3 | 3/2016 | |
| WO | 2017083694 A1 | 5/2017 | |
| WO | 2021202256 A1 | 10/2021 | |

OTHER PUBLICATIONS

International Search Report and Written Opinion, dated Feb. 14, 2020, in International Application No. PCT/US2019/064030.

Milosevic et al. (1999) "The relationship between elevated interstitial fluid pressure and blood flow in tumors—a bioengineering analysis".

Shore (2000) "Capillaroscopy and the measurement of capillary pressure".

Boucher, et al., Interstitial Pressure Gradients in Tissue-isolated and Subcutaneous Tumors: Implications for Therapy1. Cancer Res Aug. 1, 1990; 50 (15): 4478-4484.

Jain RK. Determinants of tumor blood flow: a review. Cancer Res. May 15, 1988;48(10):2641-58. PMID: 3282647.

Stylianopoulos, et al., Coevolution of solid stress and interstitial fluid pressure in tumors during progression: implications for vascular collapse. Cancer Res. Jul. 1, 2013;73(13):3833-41. doi: 10.1158/0008-5472.CAN-12-4521. Epub Apr. 30, 2013. PMID: 23633490; PMCID: PMC3702668.

* cited by examiner

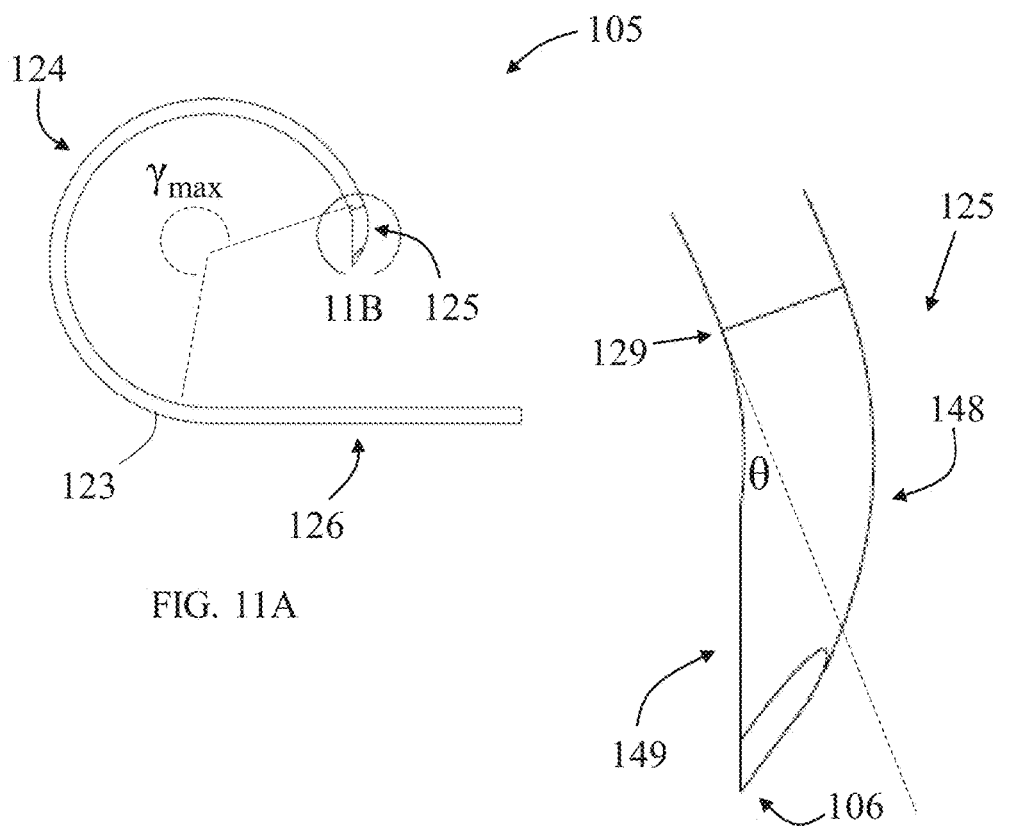
FIG. 11A
FIG. 11B
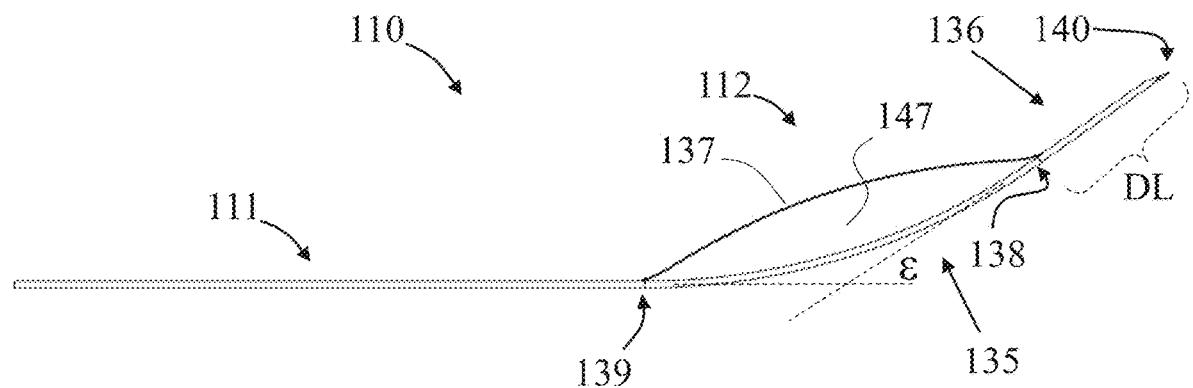
FIG. 12

DEVICE AND METHOD FOR PASSING TENSION MEMBER AROUND TISSUE MASS

CROSS-REFERENCE TO RELATED APPLICATIONS

This application is a continuation-in-part (CIP) of U.S. patent application Ser. No. 16/539,800 filed on Aug. 13, 2019 entitled: "CAUSING ISCHEMIA IN TUMORS", which claims the benefit under 35 U.S.C. § 119(e) of U.S. Provisional Patent Application No. 62/719,177 filed on Aug. 17, 2018. This application is also a continuation-in-part (CIP) of International Application No. PCT/US19/64030, filed on Dec. 2, 2019 entitled: "PASSING TENSION MEMBER AROUND TISSUE MASS", which claims the benefit under 35 U.S.C. § 119(e) of U.S. Provisional Patent Application No. 62/774,249, filed on Dec. 2, 2018, titled "APPARATUS FOR PASSING TENSION MEMBER AROUND TISSUE MASS AND METHOD OF USE THEREOF. The contents of all the above applications are fully incorporated herein by reference in their entireties, as if fully set forth herein.

FIELD OF THE INVENTION

The present disclosure, in some embodiments thereof, relates to devices and methods for passing artifacts (e.g., wires or sutures) around target tissues within a body of a subject, and more particularly, but not exclusively, to devices and methods for encompassing a tissue mass (e.g., tumor) with a tension member applicable for causing ischemia and/or necrosis thereto.

BACKGROUND OF THE INVENTION

A uterine fibroid (also referred to as a "myoma") is a benign tumor that is fed by the uterine artery and grows within the muscle tissue of the uterus. Myomas are solid fibrous tissue growing as a single nodule or in clusters and may range in size from about 1 mm to more than 20 cm in diameter. Myomas are the most frequently diagnosed tumor in the female pelvis and the most common reason for a woman to undergo hysterectomy. The prevailing symptoms of myomas include heavy menstrual bleeding, prolonged menstrual periods, pelvic pressure or pain and lower urinary tract symptoms (LUTS).

FIG. 1 illustrates an exemplary uterus with three types of fibroids. Uterine Fibroids are classified by their location which effects the symptoms they may cause and how they can be treated. Fibroids that are inside the cavity of the uterus (Submucous fibroids) often cause bleeding between periods and severe cramping. Some submucous fibroids are partially in the cavity and partially in the wall of the uterus. They too can cause heavy menstrual periods (menorrhagia), as well as bleeding between periods and are harder to remove in an hysteroscopic resection. Intramural fibroids are in the wall of the uterus and can range in size from microscopic to larger than a grapefruit. Many intramural fibroids do not cause problems until reaching a certain size. Subserous fibroids are found on the outside wall of the uterus and may even be connected to the uterus by a stalk (pedunculated fibroid). Known devices, systems, and methods for treating uterine fibroids suffer from a variety of limitations and drawbacks.

SUMMARY OF THE INVENTION

The present disclosure, in some embodiments thereof, relates to devices and methods for passing artifacts (e.g., wires or sutures) around target tissues within a body of a subject, and more particularly, but not exclusively, to devices and methods for encompassing a tissue mass (e.g., tumor) with a tension member applicable for causing ischemia and/or necrosis thereto.

In certain embodiments, there is provided an apparatus for passing a tension member around a volumetric region of an organ. The apparatus may include at least one of:

(a) a rigid outer tube comprising a sharp outer tube tip and an outer tube lumen with an outer tube opening in proximity to the outer tube tip;

(b) an inner needle comprising an elastic needle body curved at least in part thereof, the inner needle ending with a sharp needle tip and enclosing an inner needle lumen with an inner needle opening being in proximity to the needle tip, the inner needle body being configured to pass straightened through the outer tube lumen and to partially protrude via the outer tube opening, such that a protruding portion of the inner needle body is allowed to voluntarily flex to a curved form having diameter equal to or greater than diameter of the volumetric region; and (c) a tension member passer comprising a tension member passer body, sized for passing through the inner needle lumen, and a tension member pulling portion configured for engaging with a portion of the tension member and for continuously applying a pulling force to the engaged portion of the tension member when the tension member is withdrawn with the tension member passer;

In some embodiments, the apparatus is configured for forming a passage through the organ, the passage extending along a plane crossing the volumetric region from an entry point at a surface of the organ, located in front of a first side of the volumetric region, to an exit point at the surface of the organ, located in front of a second side of the volumetric portion opposite to the first side, and the apparatus is further configured for passing the tension member around the volumetric region by pulling the tension member from the exit point to the entry point through the passage.

In some embodiments, the volumetric region of the organ includes a tissue mass comprising at least a portion of a tumor.

In some embodiments, the outer tube is movable relative to a covering portion of the apparatus until the outer tube tip extends a chosen uncovered length from a distal edge of the covering portion, the distal edge is configured to resist penetration into soft tissue to inhibit insertion of the outer tube to a depth greater than the uncovered length.

In some embodiments, the elastic needle body is configured with elastic resistance to straightening within a range of 2 N to 20 N.

In some embodiments, the apparatus is configured such that the protruding portion exits the outer tube opening with a needle exit angle δ within a range of 10° to 80°, relative to the outer tube.

In some embodiments, the tension member passer body is flexible and elastic.

In some embodiments, the tension member pulling portion includes a securing member forming a loop with the tension member passer body.

In some embodiments, the tension member passer body has a curved or bent portion forming a deviated distal end portion inclined relative to remainder of the tension member passer body.

In some embodiments, the deviated tension member passer distal end portion forms with rest of the tension member passer body a deviation angle within a range of 15° to 55°.

In some embodiments, the tension member pulling portion includes a securing wire portion extending from a first location on the tension member passer body, distally to the curved or bent portion, to a second location on the tension member passer body, proximally to the curved or bent portion.

In some embodiments, the securing wire portion is similar in length to length of a segment of the tension member passer body extending from the first location to the second location.

In some embodiments, the securing wire portion is configured to undergo increased tension when the deviated tension member passer distal end portion is forced to align with rest of the tension member passer body.

In some embodiments, the deviated tension member passer distal end originates at the first location and extends in a straight form at least 10 mm in length.

In some embodiments, the curved or bent portion of the tension member passer body is configured with elastic resistance to straightening within a range of 0.1 N to 1 N.

In some embodiments, the apparatus further comprising a console, optionally formed as a handheld device.

In some embodiments, the apparatus further comprising an inner needle protrusion controller configured to operatively control advancement of the inner needle within the outer tube.

In some embodiments, the apparatus further comprising a tension member passer protrusion controller configured to operatively control advancement of the tension member passer body within the inner needle.

In certain embodiments, there is provided a method for passing a tension member around a volumetric region of an organ. The method may include at least one of the following steps (not necessarily in the listed order):

using a rigid outer tube, comprising a sharp outer tube tip and an outer tube lumen with an outer tube opening in proximity to the outer tube tip, penetrating into the organ such that the outer tube tip reaches a penetration depth;

passing an inner needle in the outer tube lumen, the inner needle includes an elastic needle body curved at least in part thereof, ending with a sharp needle tip and enclosing an inner needle lumen with an inner needle opening in proximity to the needle tip;

piercing a curved passage with the needle tip around the volumetric region with a protrusion length of a protruding portion of the inner needle body, by pushing the inner needle via the outer tube opening and allowing the protruding portion to voluntarily flex to a curved form having diameter equal to or greater than diameter of the volumetric region;

advancing a tension member passer comprising a tension member passer body and a tension member pulling portion, in the inner needle lumen and via the inner needle opening, until the tension member pulling portion exits the organ at an exit point opposing the entry point relative to the volumetric region; and drawing the tension member into and through the curved passage by pulling the tension member passer with the secured tension member.

In some embodiments, the drawing includes extending the tension member around the volumetric region such that one end of the tension member projects from the entry point and another end of the tension member projects from the exit point.

In some embodiments, the organ is an internal organ located within a body of a live subject, and the method further comprising forming a surgical route from outside the body of the subject and delivering the outer tube through the surgical route until the outer tube tip reaches the organ.

In some embodiments, the organ is a uterus.

In some embodiments, the volumetric region of the organ includes a tissue mass comprising at least a portion of a tumor.

In some embodiments, the method comprising ending the piercing with positioning the needle tip at a chosen distance from the surface of the organ, so as to form a needle tip angle between the needle tip and the surface of the internal body region.

In some embodiments, the distance is smaller than 3 cm, and/or the needle tip angle is within a range of 10° to 60°.

In some embodiments, the defining includes defining a penetration angle between the outer tube and a perpendicular line to the surface of the internal body region at the entry point, wherein the protrusion length subtends a subtended angle is at least 270° minus the penetration angle.

In some embodiments, the penetrating, the passing, the piercing, the advancing and/or the securing is repeated, each repetition is performed using a different implanted tension member, a different entry point and a different exit point.

All technical or/and scientific words, terms, or/and phrases, used herein have the same or similar meaning as commonly understood by one of ordinary skill in the art to which the invention pertains, unless otherwise specifically defined or stated herein. Exemplary embodiments of methods (steps, procedures), apparatuses (devices, systems, components thereof), equipment, and materials, illustratively described herein are exemplary and illustrative only and are not intended to be necessarily limiting. Although methods, apparatuses, equipment, and materials, equivalent or similar to those described herein can be used in practicing or/and testing embodiments of the invention, exemplary methods, apparatuses, equipment, and materials, are illustratively described below. In case of conflict, the patent specification, including definitions, will control.

BRIEF DESCRIPTION OF THE DRAWINGS

Some embodiments are herein described, by way of example only, with reference to the accompanying drawings. With specific reference now to the drawings in detail, it is stressed that the particulars shown are by way of example and for purposes of illustrative description of some embodiments of some embodiments. In this regard, the description taken together with the accompanying drawings make apparent to those skilled in the art how some embodiments may be practiced.

In the drawings:

FIGS. 11A-11B illustrate respectively a full side view and a zoom-in partial side view of an exemplary inner needle in an unstressed relaxed state, according to some embodiments;

FIG. 12 illustrates a side view of an exemplary tension member passer in an unstressed relaxed state, according to some embodiments.

DETAILED DESCRIPTION

Certain embodiments relate to devices and methods for passing artifacts (e.g., wires or sutures) around target tissues within a body of a subject, and more particularly, but not exclusively, to devices and methods for surrounding or encompassing a tissue mass (e.g., tumor) with a tension member applicable for causing ischemia and/or necrosis thereto. One or more tension members are applied, according to methods described herein, around or through a target tumor, and are put under tensioning force in a manner that triggers, supports and/or induces tumor suppression.

A "tension member", as referred to in current disclosure, relates to any flexible slender member that can withstand tension forces of at least 0.1 Kg, optionally at least 0.5 Kg, optionally at least 1 Kg, without failure (e.g., plastic deformation, tear, or breaking). In some embodiments in this disclosure, tension members cannot withstand significant compression and/or lateral forces without, breaking, collapsing or altering shape. Exemplary tension members may include medical or surgical grade wires, filaments or cables, such as sutures (e.g., biodegradable sutures) and cable ties.

In embodiments, tension members are deployed and directly affect (cause) a continuous pressure within the tumor (interstitial pressure), optionally above 22.5 mmHg, thus inhibiting blood flow into the tumor. Optionally, additionally or alternatively, tension members are deployed to path over blood vessels nourishing the tumor and are configured and taut sufficiently so as to impinge the blood vessels and block blood flowing therethrough. Blocking blood supply to the tumor for several hours leads to fibroid ischemia and eventually to necrosis of the tumor cells.

As described, the tension members can be placed around entire volume of the tumor (fibroid), optionally including portions of other tissues surrounding it, or around one or more smaller volumetric portions thereof. It may be advantageous to prefer the first option of surrounding the entire tumor (fibroid) and/or avoid passing a tension member across tumor volume especially due to sharp increase in density when entering the fibroid or the possibility the tumor is cancerous, so that puncturing therethrough increases risk of cancer spreading to surrounding tissues and blood system. Nevertheless, in some procedures it may be found advantageous to pass a tension member through the tumor such as in anatomies imposing difficulties to fully encompass the tumor.

Figure 1:
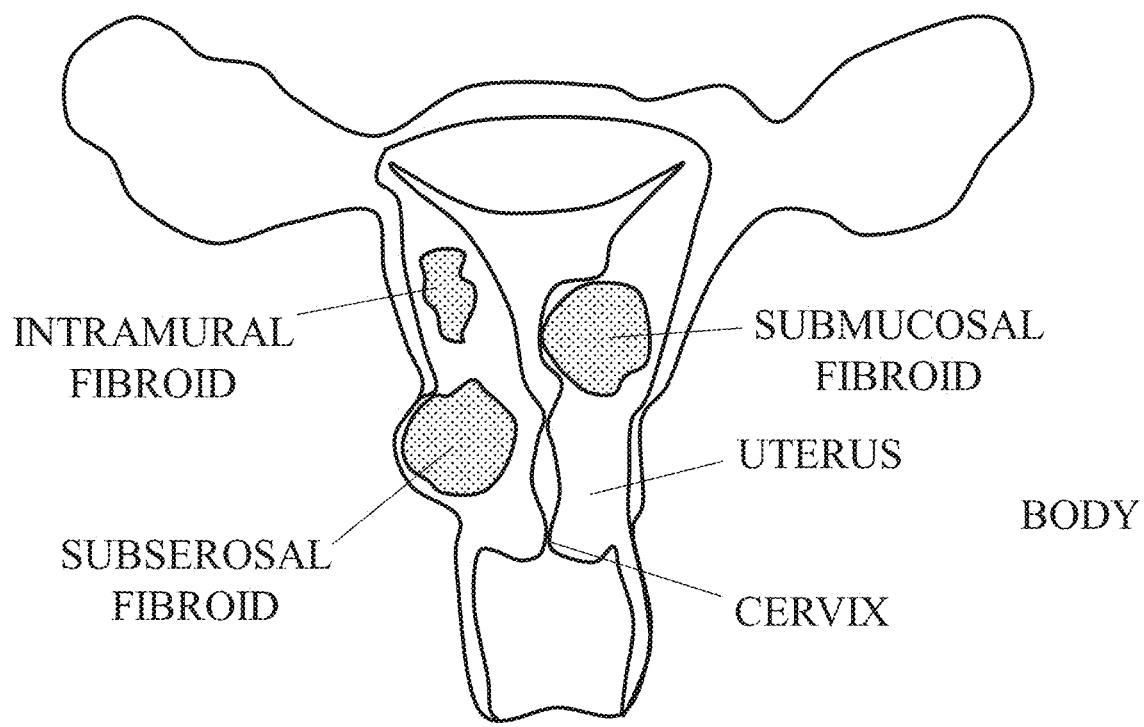
FIG. 1 schematically illustrates a frontal cross-sectional view of an exemplary female uterus having different types of fibroids growing therein.
Figures 2A, 2B:
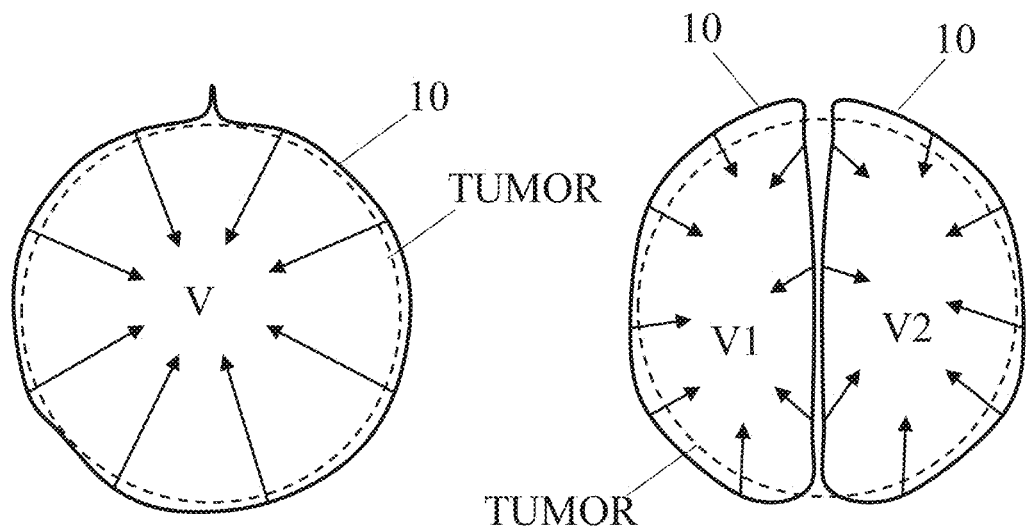
FIGS. 2A-2B schematically illustrate a cross-sectional view of an illustrative tumor being radially compressed using one or more tension members, either about entire volume of the tumor (FIG. 2A) or about a number of volumetric portions of the tumor (FIG. 2B), according to some embodiments.

FIGS. 2A-2B schematically illustrate a cross-sectional view of an exemplary target tissue mass in a form of a tumor being compressed using one or more tension members 10, either about entire volume V of the tumor (FIG. 2A) or about a number of volumetric portions V1 and V2 of the tumor (FIG. 2B). Optionally, a plurality of tension members 10 are deployed, each one encompasses more than half a circumference of the tumor or the volumetric portion, optionally more than two thirds the circumference, optionally close to a full the circumference. When under a chosen tensioning force (e.g., predetermined, measured and/or calculated), tension members 10 can be applied to affect radial compression of the surrounded volumetric portion. A plurality of tension members can be arranged around a volumetric portion of the tumor, such that the combined effect of all tension members thereto is compression towards the volumetric center of the tumor or of the volumetric portion. Tension members 10 are passed spaced apart with each other relative to a center of the tumor or the volumetric portion, optionally evenly spaced apart.

Figure 3A:
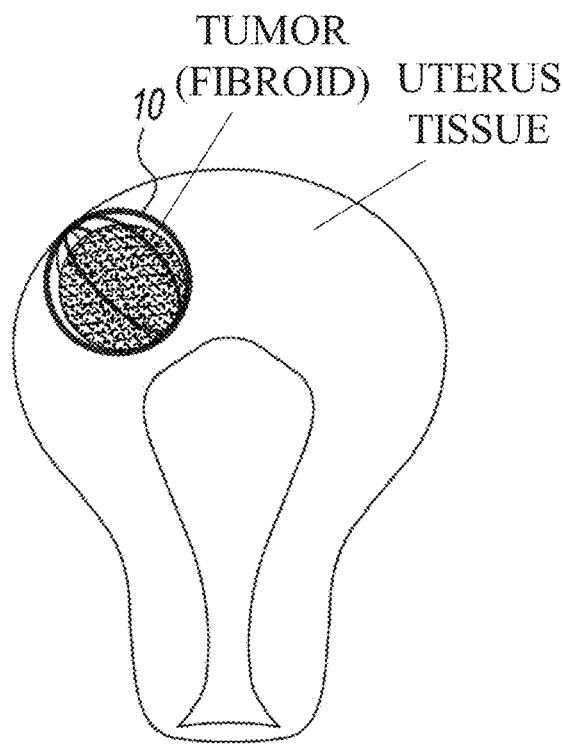
FIGS. 3A-3D schematically illustrate views of different exemplary fibroids treated using one or more tension members, according to some embodiments.
Figure 3B:
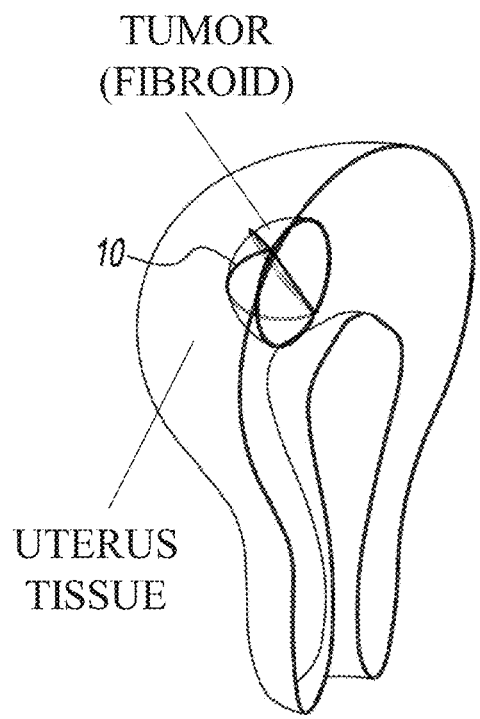
Figure 3C:
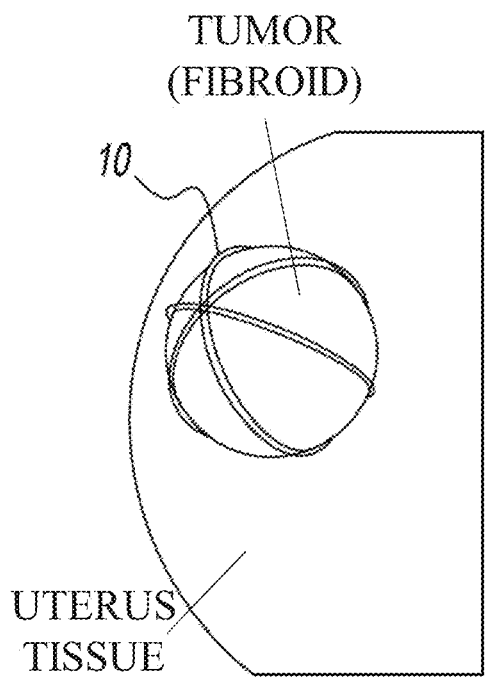
Figure 3D:
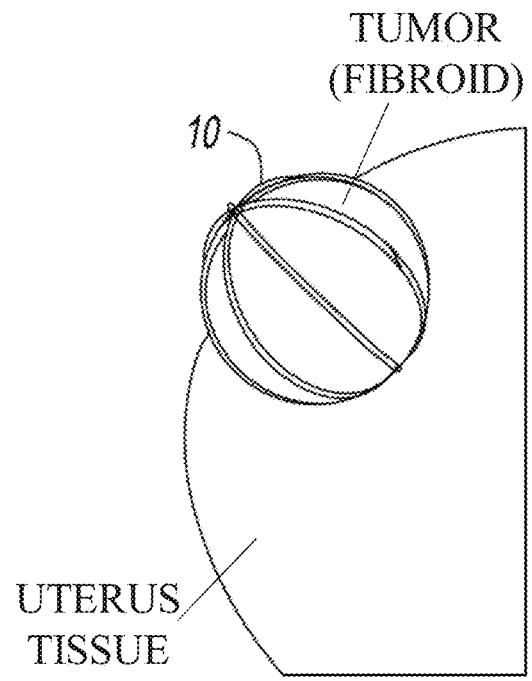

FIGS. 3A-3D schematically illustrates views of different exemplary configurations of fibroids following treatment, according to some embodiments. In some embodiments, as shown in FIG. 3A, one or more tension members 10 may be provided (implanted) around the fibroid when passing partially or fully through a (healthy) uterus tissue surrounding the fibroid, particularly in cases of intramural fibroids. Optionally, additionally or alternatively, one or more tension members 10 may be provided through the fibroid tissue, such as through its center or in proximity thereto, as shown in FIG. 3B. The number of tension members used can be determined according to need or tumor size or type, for example two tension members, three tension members (FIG. 3C), four tension members (FIG. 3D), five tension members, six tension members, eight tension members, or more. In some embodiments, one or more tension members 10 can be secured to the tumor and/or surrounding tissue by way of suturing or tying around the tumor (as shown in FIGS. 2A and 3A, for example) or a volumetric portion thereof (as shown in FIG. 2B, for example).

Figure 4A:
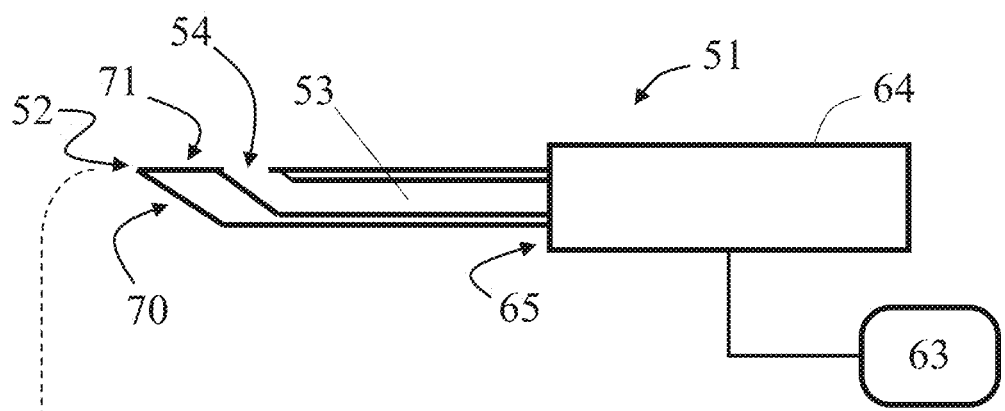
FIGS. 4A-4C schematically illustrate side cross-sectional views of components of an exemplary apparatus for passing a tension member around a tissue mass, according to some embodiments.
Figure 4B:
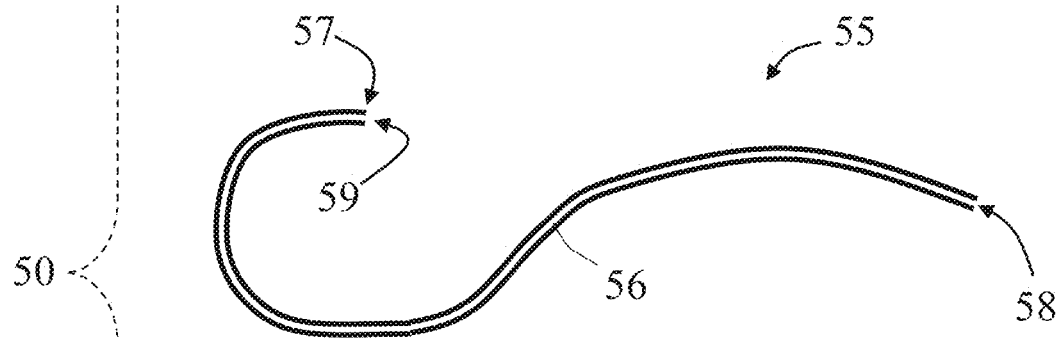
Figure 4C:
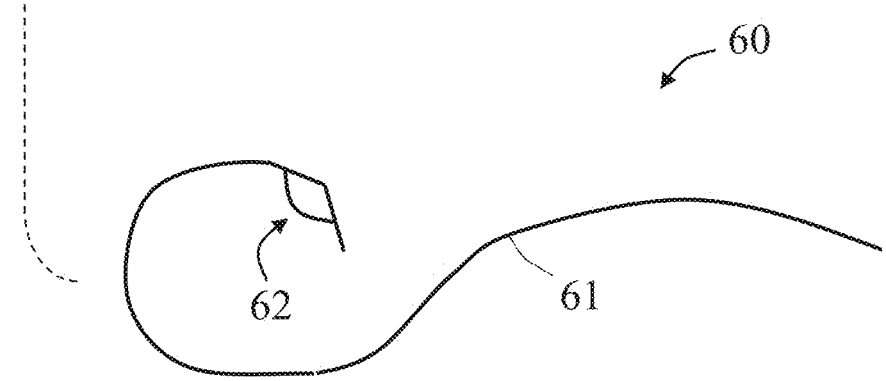
Figure 5A:
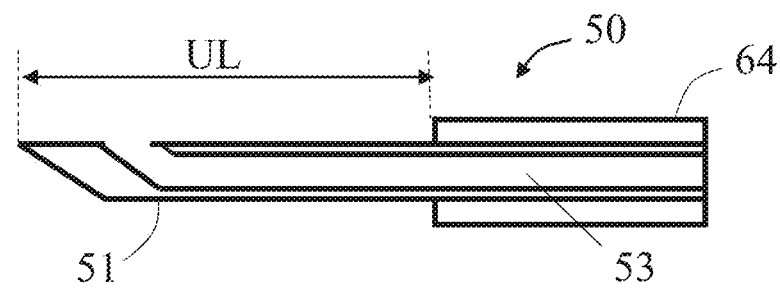
FIGS. 5A-5D schematically illustrate exemplary scenarios representing steps in an exemplary method for using the exemplary apparatus referred to in FIGS. 4A-4C, according to some embodiments.

FIGS. 4A-4C schematically illustrate side cross-sectional views of components of an exemplary apparatus 50 for passing a tension member around a tissue mass. FIGS. 5A-5D schematically illustrate exemplary scenarios representing steps in an exemplary method for using apparatus 50. FIG. 4A shows a rigid outer tube 51 which comprises a sharp outer tube tip 52 and an outer tube lumen 53 opened to an outer tube opening 54 formed as a lateral opening in proximity to outer tube tip 52. Outer tube 51 includes a bevel configured with a bevel face 70 opposing a straight side 71 that encloses outer tube side opening 54. An outer tube uncovering mechanism 63 is provided with outer tube 51 and configured for fixating a chosen uncovered length UL of outer tube 51 relative to a tube cover 64 covering remaining length of outer tube 51 (as shown in FIG. 5A). Tube cover 64 has a distal edge 65 (e.g., outer diameter), being wider substantially from boundary (e.g., outer diameter) of outer tube 51, configured to resist penetration of outer tube 51 into soft tissue beyond a depth penetrable with uncovered length UL.

Figure 5B:
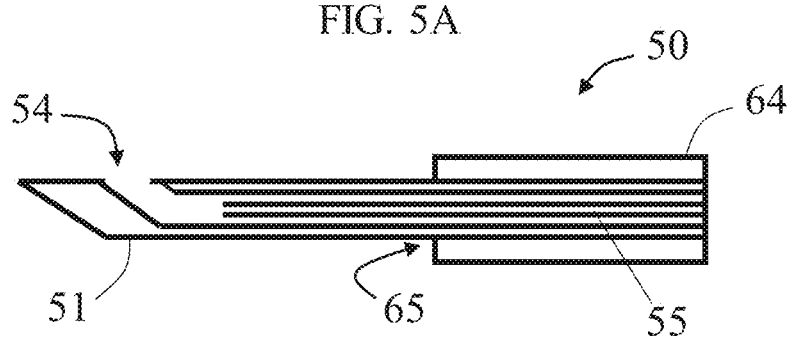
Figure 5C:
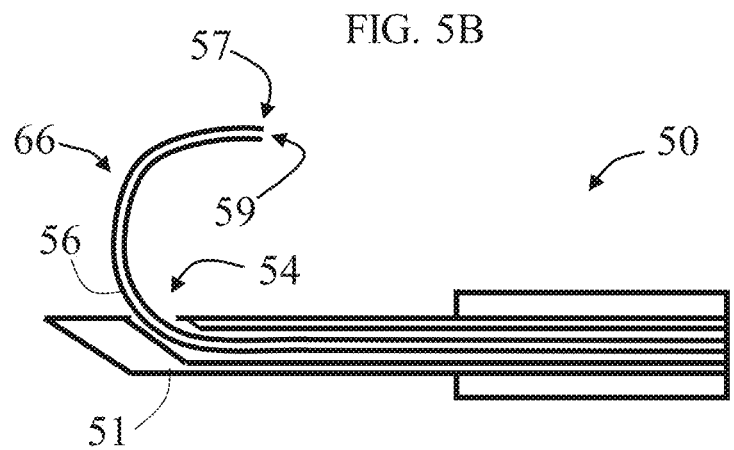

FIG. 4B shows an inner needle 55, in an unstressed relaxed length (in which no external forces or internal stresses are applied in a manner sufficient to deform its size and/or shape, at least not significantly and/or visually), which comprises an elastic needle body 56 ending with a sharp needle tip 57 and enclosing an inner needle lumen 58. Inner needle lumen 58 is opened to an inner needle opening 59 in proximity to needle tip 57. Inner needle 55 is configured to pass straightened through outer tube lumen 53 due to its flexibility and the constraining rigid boundaries of outer tube lumen 53 affected by surrounding wall of outer tube 51 (As shown in FIG. 5B). Once inner needle 51 partially protrudes via outer tube opening 54, the protruding portion 66 of inner needle 51 can voluntarily flex (by its elasticity properties) to a curved form, as shown in FIG. 5C. When in its curved form, inner needle 55 is configured to pierce a curved passage around a target tissue mass, by rotationally advancing through the soft tissue surrounding the tissue mass, when pushed via outer tube opening 54.

Since that apparatus 50 is configured to pass tension members around a tissue mass such as fibroids, which can be of different sizes, shapes and/or depth (relative to surface of an internal body organ, for example), it may be advantageous in some scenarios to preset a penetration length, from within a range of allowed selectively fixable lengths, which is deriving from, and equal to, the uncovered length UL. This measured penetration of outer tube 51 will allow outer tube opening 54 to be positioned near the outer periphery of the target tissue mass, such that the protruding portion 66 of inner needle 55 can be curved beyond and around the distal boundaries of the tissue mass in proximity thereto. In some embodiments, uncovered length UL is determined in accordance with positioning outer tube opening 54 in proximity to a chosen part of the tissue mass, for example near its middle. Predetermining uncovered length UL may be performed in advance using analysis of invasive or noninvasive imagery.

Figure 5D:
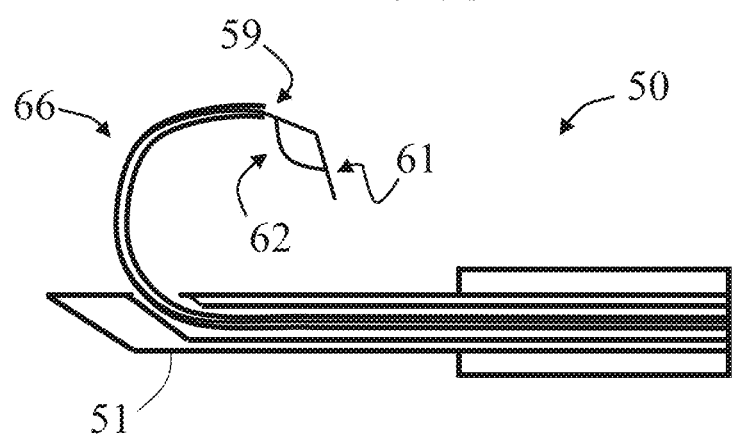

FIG. 4C shows a tension member passer 60, in an unstressed relaxed state, which comprises a tension member passer body 61, sized for passing through inner needle lumen 58, and a tension member passer securing member 62, optionally a wire forming a snare-like structure with tension member passer body 61, configured for securing a portion of a tension member to the tension member passer body 61. As shown in FIG. 5D, tension member passer 60 is advanced through inner needle lumen 58 until tension member passer securing member 62 protrudes (fully or partially) from inner needle opening 59. As will be described in details below, a tension member can be secured to tension member passer body 61 with tension member passer securing member 62, then the tension member can be withdrawn towards and/or into outer tube lumen 53 (via outer tube opening 54) by pulling it with tension member passer 60, optionally together with inner needle 55.

FIGS. 6A-6H schematically illustrate exemplary scenarios representing optional steps in an illustrative method for passing a tension member S around a volumetric region VR of an organ. Volumetric region VR includes a tissue mass TM optionally comprising at least a portion of a tumor. The organ, optionally a uterus of a female subject, is illustrated and referred to in part thereof as a body region BR. In various embodiments, the method is intended for facilitating selective volumetric compression of volumetric region VR and/or tissue mass TM to increase pressure (optionally an interstitial pressure) within the volumetric region VR above a threshold level that is sufficient to cause ischemia of tissue mass TM or a tumor therein; and maintaining the pressure above the threshold level for a period sufficient to permit at least a portion of the volumetric region VR to necrotize due to the ischemia.

The volumetric region VR is optionally circumscribed with at least one device of foreign origin relative to the patient, for example a tension member such as a surgical wire, wherein the volumetrically compressing the volumetric region VR and maintaining the elevated internal pressure are achieved via the at least one device. The treated tissue mass TM is optionally a uterine fibroid, and may be one of intramural, subserous or submucosal with respect to the organ it resides in. Optionally, at least a portion of the tissue mass TM is situated intramurally within the organ, and wherein passing the tension member within the organ comprises passing the tension member through an intramural portion of the organ. Passing the tension member through the intramural portion of the organ may comprise passing the tension member around the at least a portion of the tissue mass TM that is situated intramurally within the organ. In some such scenarios, passing the tension member within the organ may comprise passing the tension member exclusively through the intramural portion of the organ and/or the tissue mass TM between the entry point/opening and the exit point/opening.

In order to reach the surface of the organ and treat the tissue mass TM, a surgical access to the organ may be first created from outside the body, which may be formed using minimally invasive techniques or by way of open surgery, for example. At least one of the basic method steps can be performed via the surgical access. The entry point to the organ can be located at a first location on or adjacent to the tissue mass and the exit point can be located at a second location on or adjacent to the tissue mass spaced from the first location, such that the tissue mass TM is located between the entry and exit openings.

Prior to passing the tension member, a passage can be formed around the volumetric region VR and tissue mass TM between the entry and exit points, optionally also forming the entry and exit points (openings), such that the passing can be performed mostly or entirely within the passage, optionally by way of pulling the tension member via the exit point towards the entry point. The passage may be formed using apparatus 50 or any other applicable apparatus or mechanism. For example, an outer tube can be used to create the entry point and positioned through the entry point (opening) into the organ, in proximity to the tissue mass. A curved needle can then be advanced through a lumen of the outer tube around the volumetric region VR.

The volumetric region may be predetermined by a user (practitioner, physician, surgeon, etc.) and passing the tension member may be performed in close fit to and around the tissue mass. Determining the volumetric region may include determining entry and exit points to and from the organ in relation to the tissue mass, and possibly also a particular plane crossing the volumetric region VR and/or tissue mass TM. Passing the tension member may be along a predetermined passage line between the entry point and the exit point. The passage is configured to extend along a plane crossing the volumetric region from an entry point at a surface of the organ, located in front of a first side of the volumetric region, to an exit point at the surface of the organ, located in front of a second side of the volumetric portion opposite to the first side of the organ. The passage line optionally projects across one or more blood vessels feeding the tumor, such that the tightening of the tension member directly causes occlusion of the blood vessels, such as previously discussed.

Passing the tension member may include encompassing more than half a circumference of the tumor with the tension member, and/or it may include winding the tension member or a plurality of additional tension members along separate paths and/or planes around the volumetric region. In case of an additional volumetric region encompasses at least another portion of the tumor, passing the tension member may also include deploying a plurality of windings around the additional volumetric region. The volumetric region optionally encompasses most of a volume of the tissue mass, or its entirety.

The tension member optionally comprises a flexible strip or a wire, such as a suture wire, and may be formed of at least one of implant-grade metal alloy, implant-grade polymer, implant-grade textile, and biodegradable material. In certain embodiments, the tension member is configured with a yield strength or a maximal tension force of at least 25 N (newtons) in order not to prevent failing during tumor compression. Optionally the tension member is configured to yield above about 80 newton or about 100 N (newton) before it can cause cutting in organ tissues resulting from tumor compression by the tension member. Optionally, the tension member is formed as a biodegradable suture wire and is configured to yield under tensioning forces below 25 N (newtons) after the tumor tissues are ischemic or necrotic, for example after a few weeks or months.

Figure 6A:
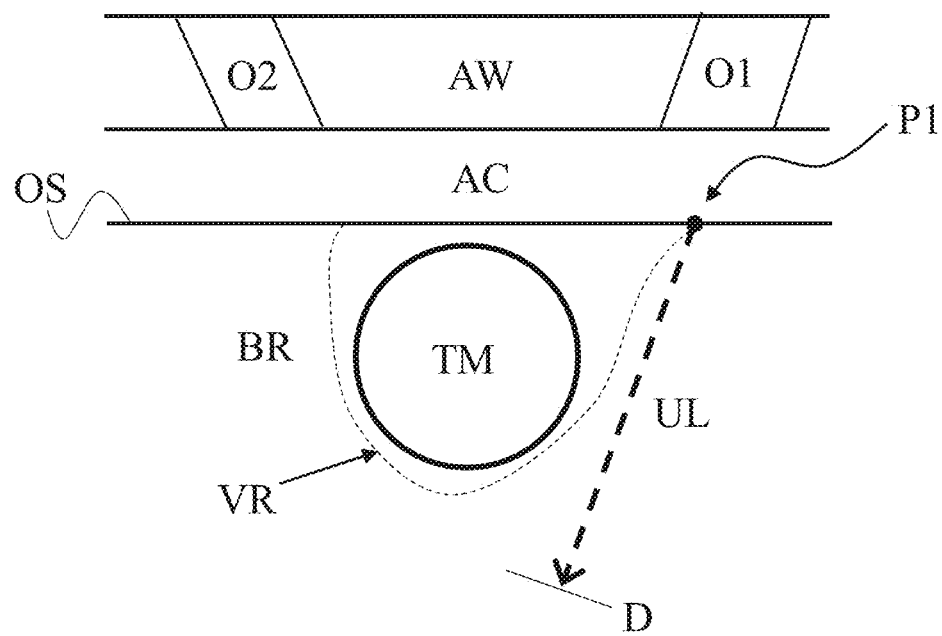
FIGS. 6A-6H schematically illustrate exemplary scenarios representing steps in an exemplary method for passing a tension member around a tissue mass within an internal body region, using the exemplary apparatus referred to in FIGS. 4A-4C, according to some embodiments.

With further reference to FIGS. 6A-6H demonstrate various stages of an illustrative method of passing a tension member S, configured as wire (e.g., suture), around a tissue mass TM (e.g., tumor) within an organ or a body region BR. FIG. 6A illustrates an exemplary scenario in which one or more surgical (e.g., minimally invasive or laparoscopic) openings, O1 and O2, are formed to an abdominal wall AW for creating separate surgical passages into an abdominal cavity AC and therethrough to outer surface OS of internal body region BR. Either one of openings O1 and O2 may be a transcutaneous cut or a fixed passage maintained by an artifact such as a trocar or a cannula.

In an optional preliminary step, the user (surgeon, practitioner, etc.) may determine a desired orientation for a tension member to pass within body region BR with respect to tissue mass TM. Such a calculated, selected, and/or predetermined orientation may be spatial or two-dimensional. The user may determine an at least one volumetric region VR which encompasses at least a portion of tissue mass TM. Optionally, alternatively or additionally, the user determines a plane crossing or passing through tissue mass TM on which points of entry and exit to and from the body region BR will be made. Optionally, a penetration depth D is defined, taken from an entry point P1 at surface OS relative to boundaries of tissue mass TM.

Figure 6B:
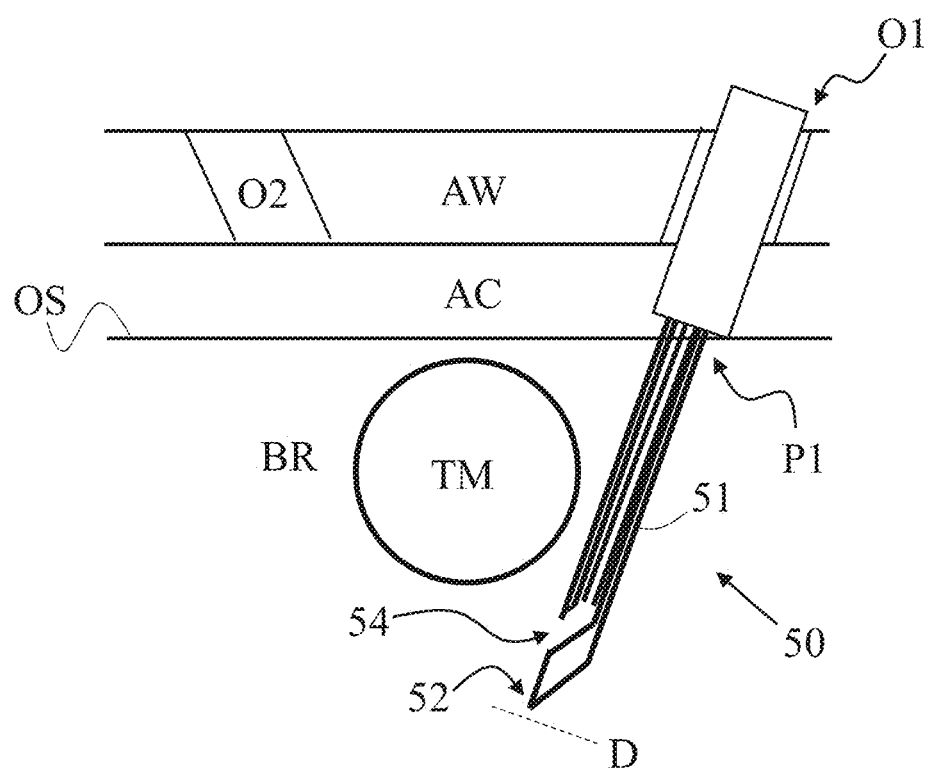

A suture passing mechanism, optionally part of apparatus 50, is then put into use. In some instances, a chosen uncovered length UL of outer tube 51 is first set or fixated, which uncovered length UL can be substantially equal to penetration depth D, by adequately withdrawing tube cover 409 (as described above). Alternatively, uncovered length UL is fixed and predetermined. Apparatus 50 is then passed via first laparoscopic opening O1 and then pressed with sharp outer tube tip 52 at a chosen direction against surface OS until penetrating the soft tissue of the body region BR in proximity to tissue mass TM (FIG. 6B). By doing so, tip 52 forms entry point P1 and a first segment of a surgical passage within body region BR around tissue mass TM and/or volumetric portion VR. Apparatus 50 is pushed distally until outer tube tip 52 reaches the predefined penetration depth D, or possibly slightly beyond it, or until outer tube opening 54 is positioned a chosen distance (e.g., a chosen proximal distance) from a distal boundary of the tissue mass TM. For example, the opening 54 may, in some instances, desirably be positioned at a depth that corresponds to about the middle of tissue mass TM (i.e., a distance substantially equal to the radius of tissue mass TM, as spaced from a distal boundary of the tumor). In some embodiments, apparatus 50, or particularly outer tube 51 and/or inner needle 55, is of a chosen size out of a variety of sizes, such that the length between outer tube opening 54 and outer tube tip 52 is about the size of tissue mass TM radius. In such embodiments, penetration depth D will be determined so that if outer tube tip 52 is in proximity to distal boundary of tissue mass TM then outer tube opening 54 is also in proximity to middle of tissue mass TM.

Stated otherwise, in some instances, a plurality of inner needles 55 may be provided. Each needle 55 may have has a pre-curved region with a length and/or radius of curvature that differs from the lengths and/or radii of curvature of the remaining options. A user may choose one inner needle 55 out of the available plurality that will form a passageway of a desired shape, size, and/or orientation around the tumor. In some instances, the outer needle 55 is provided separately from one or more of the inner needles 55. In other instances, the outer needle or tube 51 and a plurality of inner needles 55 are provided together (e.g., are provided in a unitary kit).

Figure 6C:
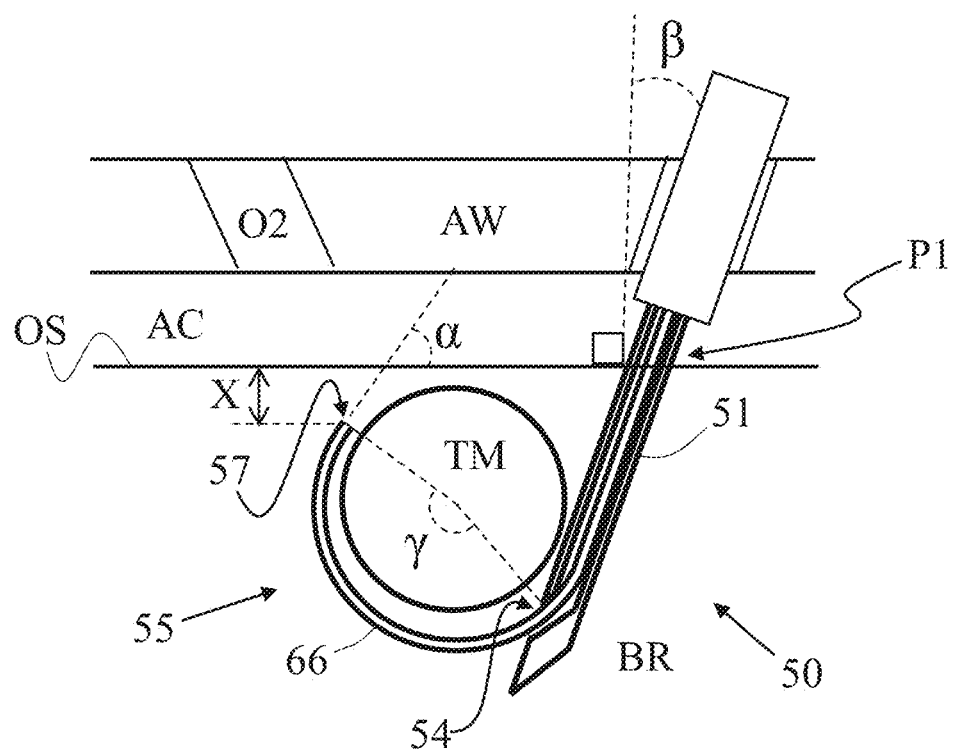

As shown in FIG. 6C, inner needle 55 can then be passed in outer tube lumen 58 in a travel length sufficiently for extending protrusion portion 66 in a chosen protrusion length via outer tube opening 54. Accordingly, by pushing inner needle 55 via outer tube opening 54, the surgical passage made in body region BR is extended with a curved segment pierced with needle tip 57 around volumetric region VR and/or tissue mass TM, along span of protrusion portion 66. As described above, protruding portion 66 naturally flexes from a straightened form to regain a preformed curved form; and the curved portion can advance along a curved path through soft tissue surrounding the tissue mass TM so as to facilitate formation of (e.g., via piercing through tissue) the curved passage segment.

Inner needle 55 protrudes from outer tube opening 54 at predetermined distance proximally to penetration depth D (e.g., equal to about the size of tissue mass TM radius). Therefore, since outer tube opening 54 is configured as lateral opening, soft tissue penetrated with outer tube 51 is prevented from entering outer tube lumen 53; the inclined exit of inner needle 55 immediately at boundary of outer tube opening 54 increases the initial piercing power of inner needle 55 into soft tissue surrounding outer tube opening 54, relative to tangential exit; and the portion of outer tube 51 between outer tube opening 54 and outer tube tip 52 increases resistance of outer tube 51 to motions in reaction to inner needle 55 engagement with soft tissue laterally thereto.

Once the penetration depth D is determined, and optionally after outer tube 51 is accordingly positioned in internal body region BR along tissue mass TM, the chosen positioning of inner needle tip 57 and protrusion length of inner needle protruding portion 66 can be determined. In some embodiments, inner needle protruding portion 66 is required to surround a chosen portion of tissue mass TM perimeter (measured in an angle γ subtended by inner needle protruding portion 66), and needle tip 57 is required to be positioned at a chosen distance X from internal body region surface OS and/or at a chosen needle tip angle α formed between tangent projection of inner needle 55 at needle tip 57 and internal body region surface OS. In some embodiments, all dimensions are configured relative to largest cross section of tissue mass TM in a certain direction.

Figure 6D:
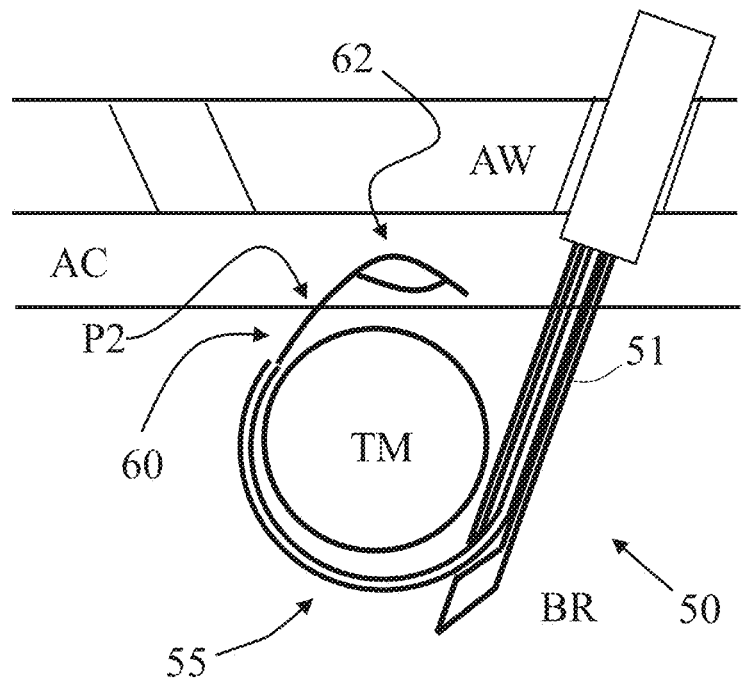

In some embodiments, needle tip angle α is equal to or smaller than 90°, optionally taken within a range of about 10° to about 60°, optionally about 30° to about 45°, so that further penetration by tension member passer 60 until emerging into abdominal cavity AC with tension member passer securing member 62 (as shown in FIG. 6D) will be sufficiently close (e.g., within distance of about 5 cm or less) to entry point P1, yet without risking further curving of tension member passer 60 within internal body region BR and emerging back into abdominal cavity AC. Similarly, distance X is optionally smaller than 5 cm, optionally taken within a range of 0.5 cm to 3 cm, optionally 0.5 cm to 1.5 cm.

Subtended angle γ of inner needle protruding portion 66 is determined according to the target positioning of needle tip 57 relative to entry point P1 and tissue mass TM, as described, and it is also dependent on the magnitude of outer tube 51 penetration angle β (measured relative to perpendicular line to internal body region surface OS at entry point P1). Optionally, Subtended angle γ is greater than 180°-β, optionally particularly at least 225°-β, optionally particularly at least 270°-β.

After formation of the curved portion of the path via the inner needle 55, the tension member passer 60, which may optionally be pre-loaded within inner needle 55, is advanced through inner needle lumen 58 and out of inner needle opening 59 until securing member 62 portion exits internal body region BR at an exit point P2, which can be spaced from (e.g., opposingly located relative to) entry point P1, relative to tissue mass TM (FIG. 6D). Stated otherwise, the entry and exit points P1, P2 may be at opposing sides of the tumor along a surface of the organ (e.g., uterus). As described above, location of exit point P2 can be predetermined or at least selected or determined in advance in correlation with distance and orientation of inner needle tip 57 relative to internal body region outer surface OS. In some instances, it can be desirable for the exit point P2 to be within a range of 2 cm to 5 cm from entry point P1 in order to: keep both points P1, P2 within the user's visual range (e.g., using an endoscope or camera positioned in abdominal cavity AC via a separate channel or surgical opening); in some instances, sufficiently distant from adjacent organs which can be harmed if unintentionally penetrated; and/or effectively tension both ends of tension member (suture) S around tissue mass TM which ends of the tension member S will ultimately emerge from points P1 and P2, as shown in FIG. 6H, for example.

Figure 6E:
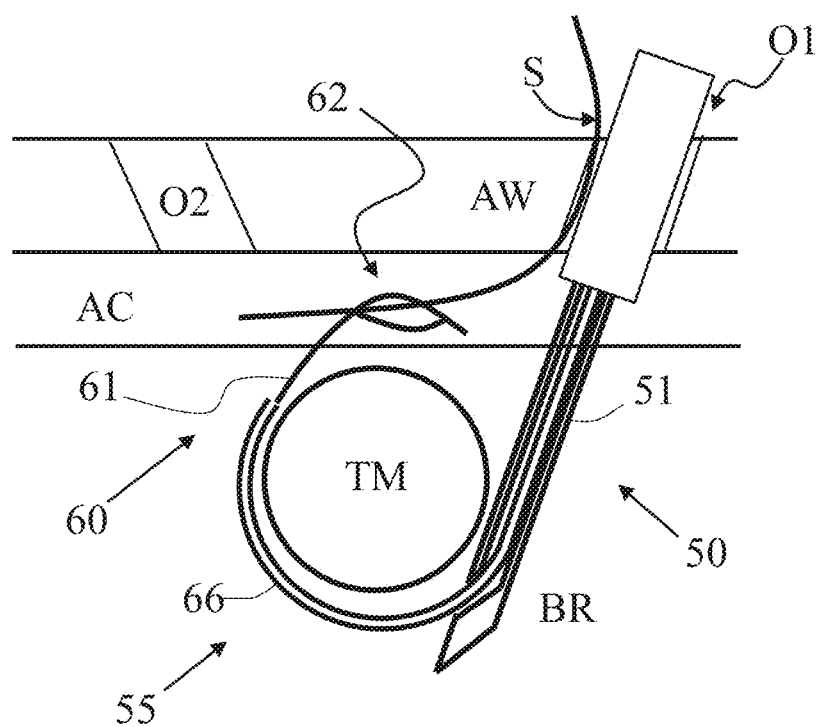
Figure 6F:
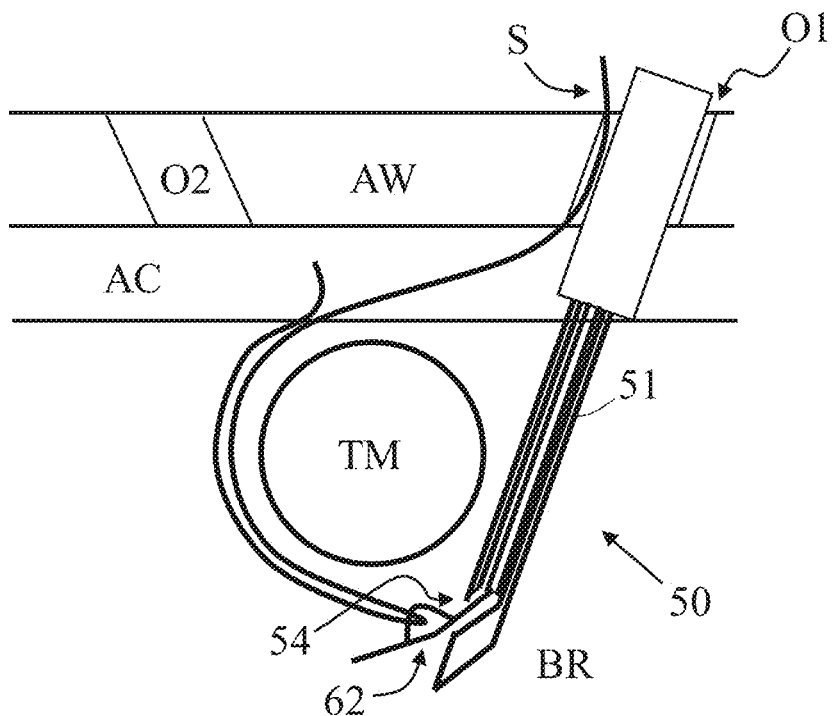

In certain embodiments, tension member S is inserted into abdominal cavity AC through first or second surgical opening O1, O2 (in this example, first opening O1, alongside, through or with apparatus 50) as shown in FIG. 6E. A portion of tension member S is then passed through the lumen of securing member 62, optionally using a surgical tool such as surgical grasper which may be operated via second opening O2, or via first opening O1, or provided with or via apparatus 50. The tension member S therefore can be coupled or secured to tension member passer body 61 and drawn towards and/or into inner needle lumen 58 and/or outer tube lumen 53 by pulling tension member passer 60 with tension member S secured thereto (FIG. 6F). In some instances, a grip of the securing member 62 on the tension member S can increase or be enhanced as the securing member 62 is drawn into the lumen of the tube 51 and/or the inner needle 55, as a loop formed thereby may be resiliently compressed when passing into or through the lumens thereof.

Figure 6G:
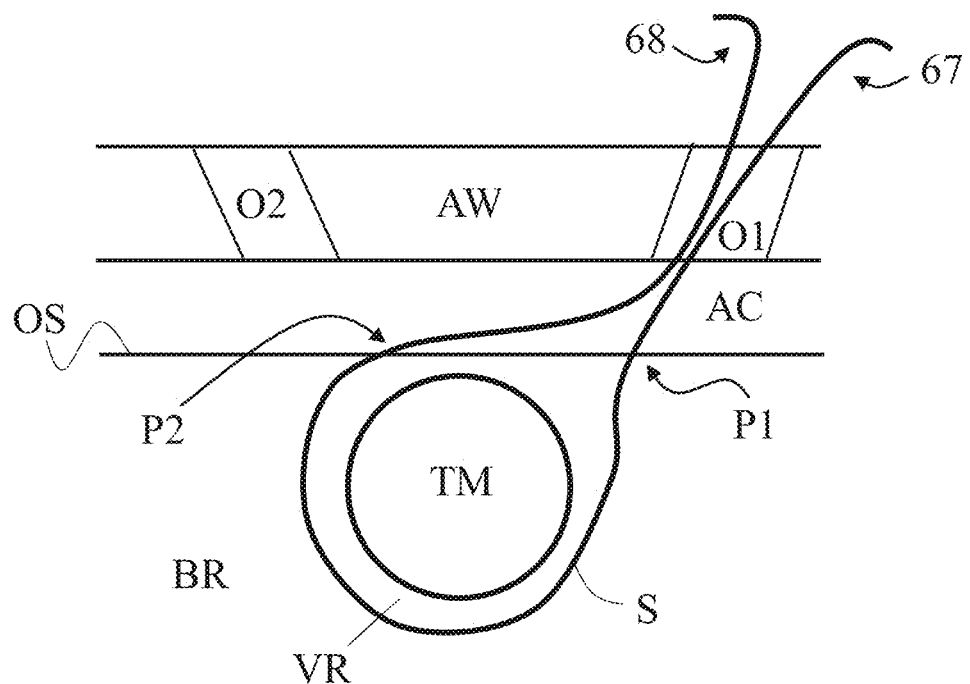
Figure 6H:
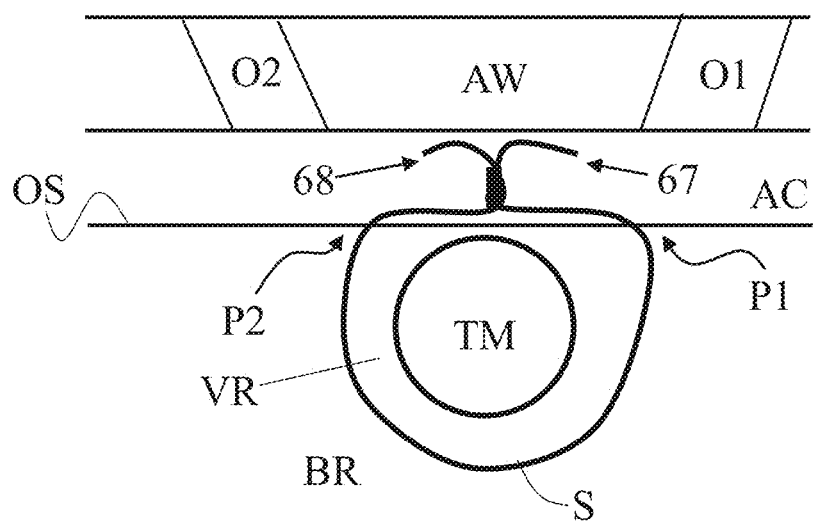

Apparatus 50 is then pulled out from inner body region BR while drawing the captured tension member S, and then removed from patient's body. As a result, tension member S can be left extended around volumetric region and/or tissue mass TM such that one portion or end 67 of tension member S extends from entry point P1 through abdominal cavity AC and out of patient's body, and another portion or end 68 of tension member S extends from exit point P2 through abdominal cavity AC and out of patient's body (FIG. 6G). The two portions 67 and 68 of tension member S can be further manipulated from outside the body, such as for tightening (and/or tumor compressing) and securing (and/or maintaining tumor compression) of tension member S, as shown in FIG. 6H, for example, either by connecting together its two ends 67 and 68 (e.g., by way of tying) and/or by connecting them using an additional component or material (e.g., by way of crimping a metal ring around both ends 67 and 68). In some embodiments, the tension member S loop is fastened while taut thereby affecting continuous compression to target tissue TM. Residual length of tension member S can be trimmed and removed as needed. Tension member S can be made of biodegradable material and left implanted indefinitely.

Some or all steps can repeated, each repetition performed using a different implanted suture, a different entry point and a different exit point.

Figure 7A:
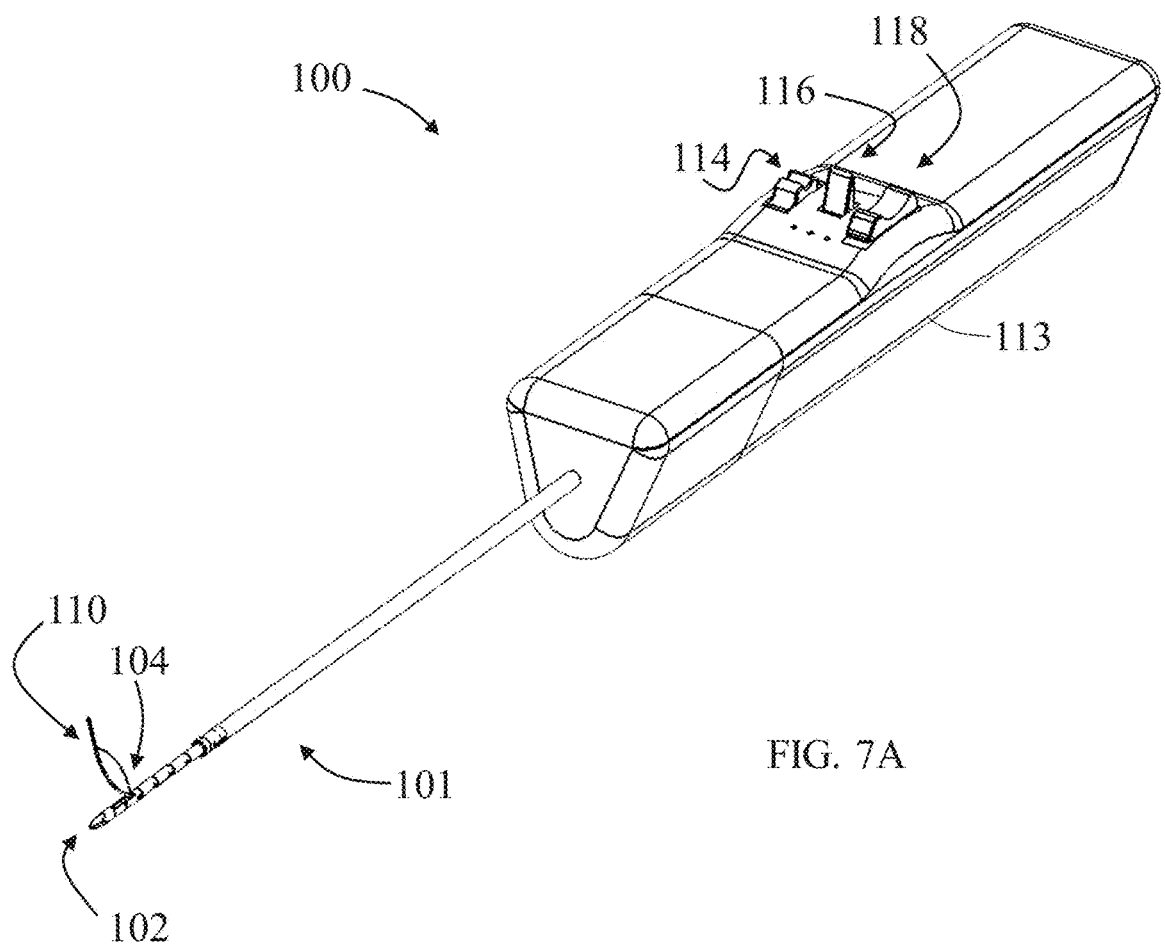
FIGS. 7A-7B illustrate respectively an isometric view and a partial side cross-sectional view of an exemplary apparatus for passing a tension member around a tissue mass, according to some embodiments.
Figure 7B:
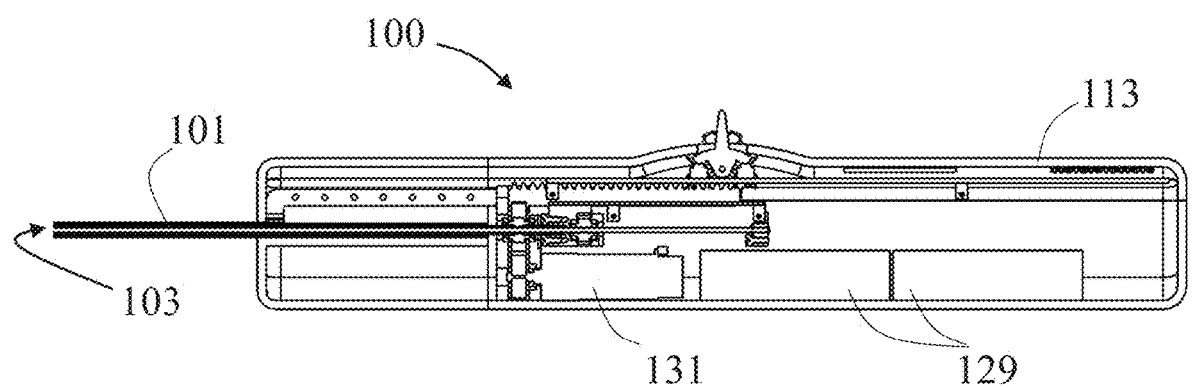

FIGS. 7A-7B illustrate respectively an isometric view and a partial side cross-sectional view of an exemplary apparatus 100 for passing a tension member around a tissue mass. Apparatus 100 is optionally an exemplary implementation or variation of apparatus 50 described above, and it may include some or all embodiments and features of apparatus 50. Apparatus 100 includes a rigid outer tube 101 (shown in greater detail in FIGS. 8A and 8B) comprising a sharp outer tube tip 102 and an outer tube lumen 103 opened to an outer tube opening 104 in proximity to outer tube tip 102. Outer tube 101 is straight and formed of stainless steel, and has a total length within 20 cm to 40 cm. Outer tube lumen 103 has dimeter within range of 3 mm to 12 mm, optionally about 5 mm. Outer tube opening 104 is provided at the side of outer tube 101 (i.e., lateral opening), it is oval in shape with distal portion thereof optionally adjoining with outer tube lumen via a slope, so that inner needle can slide its way to protrude therethrough. Outer tube opening 104 is located at a distance from outer tube tip 102 being about the size of a target tissue mass radius, therefore different outer tube sizes can be chosen according to different tissue masses sizes, or that the distance between outer tube opening 104 and outer tube tip 102 can be selectively fixated accordingly.

Figure 9A:
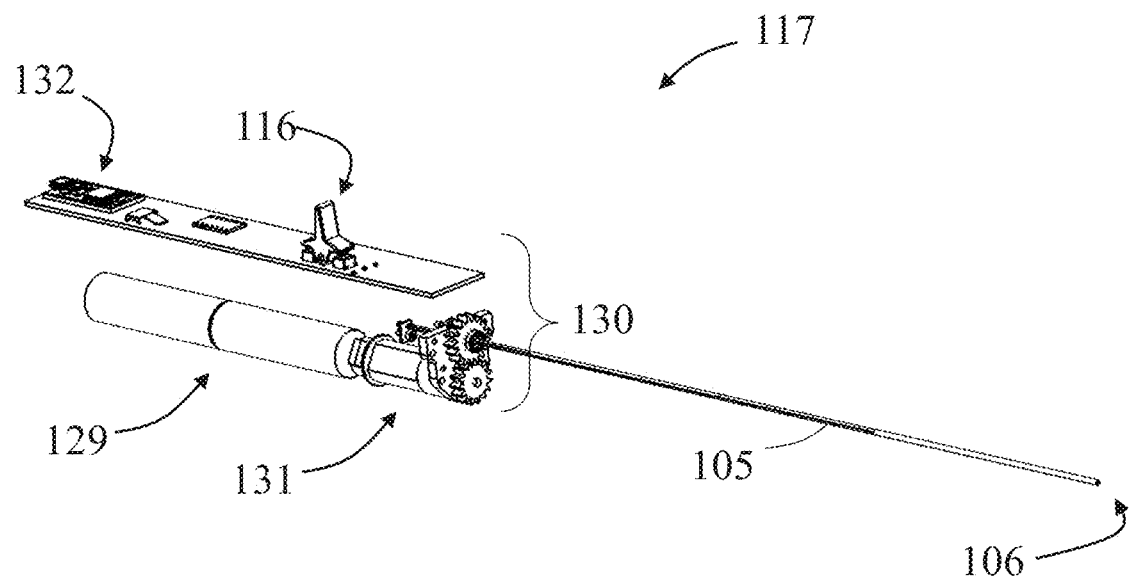
FIGS. 9A-9B illustrate respectively a full isometric view and a zoom-in partial isometric view of an inner needle advancing mechanism provided in the exemplary apparatus shown in FIG. 7A, according to some embodiments.

Apparatus 100 includes an inner needle 105 (shown in detail in FIGS. 9A and 11A, for example) comprising an elastic needle body 123 ending with a sharp needle tip 106 and enclosing an inner needle lumen opened to an inner needle opening (similar to inner needle lumen and opening, 58 and 59, of apparatus 50) adjacent to needle tip 106. Inner needle 105 is configured to pass straightened (as shown in FIG. 9A) through outer tube lumen 103 and to partially protrude via outer tube opening 104, such that a protruding portion 109 (shown in FIG. 13C, for example) of inner needle 105 is allowed to voluntarily flex to a curved form configured for rotationally advancing through soft tissue surrounding the tissue mass, for piercing a curved passage around the tissue mass (as described above).

Apparatus 100 also includes a tension member passer 110 (shown in detail in FIGS. 10A and 12, for example) comprising a tension member passer body 111, sized for passing through inner needle lumen, and a tension member passer pulling portion or securing member 112 configured for securing a portion of a tension member (e.g., suture) to the tension member passer body 111.

Figure 10A:
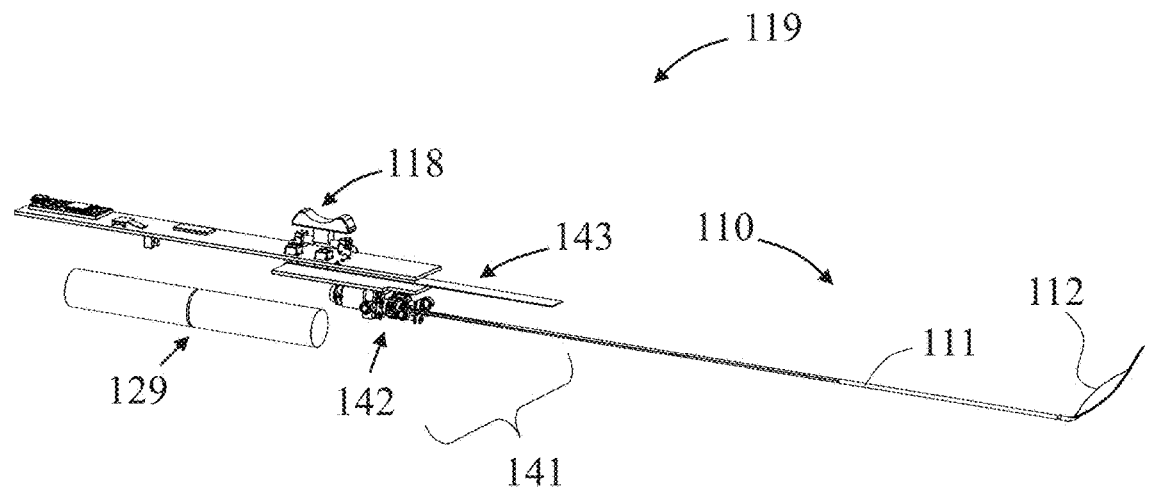
FIGS. 10A-10B illustrate respectively a full isometric view and a zoom-in partial isometric view of a tension member passer advancing mechanism provided in the exemplary apparatus shown in FIG. 7A, according to some embodiments.

Apparatus 100 further includes a console 113 in a form of a handheld device, and is equipped with a first control 114 formed as a knob for activating an outer tube uncovering mechanism 115 (shown in detail in FIG. 8A, for example), a second control 116 formed as a switch for activating an inner needle advancing mechanism 117 (shown in detail in FIG. 9A, for example), and a third control 118 formed as a switch for activating an inner needle advancing mechanism 119 (shown in detail in FIG. 10A, for example).

Figure 8A:
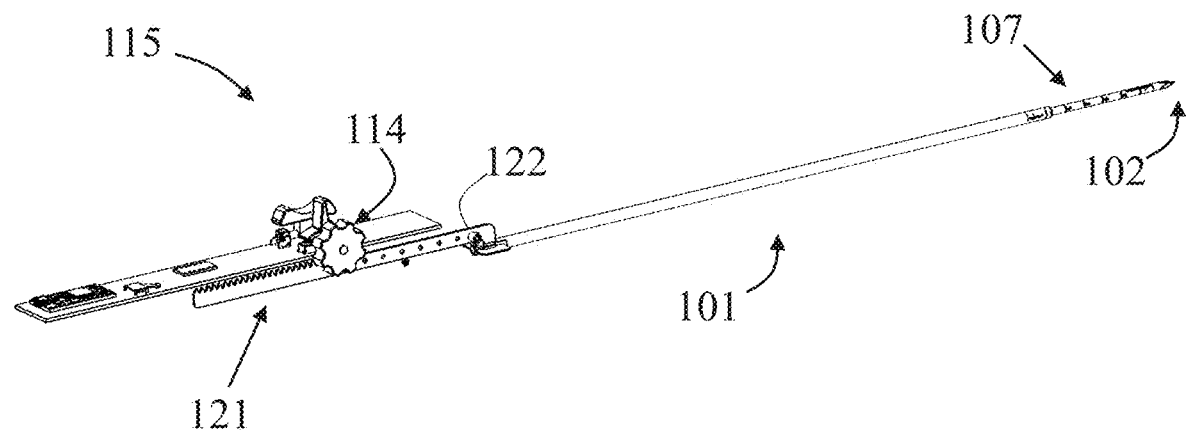
FIGS. 8A-8B illustrate respectively a full isometric view and a zoom-in partial isometric view of an exemplary outer tube uncovering mechanism provided in the exemplary apparatus shown in FIG. 7A, according to some embodiments.
Figure 8B:
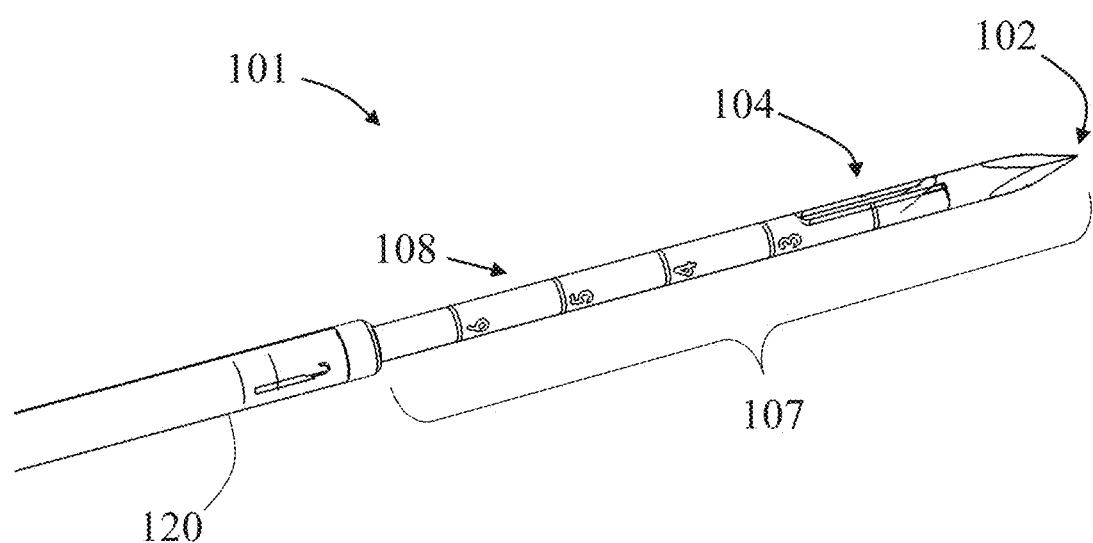

FIGS. 8A-8B illustrate respectively a full isometric view and a zoom-in partial isometric view of outer tube uncovering mechanism 115 provided in apparatus 100. Outer tube uncovering mechanism 115 is configured for fixating a chosen uncovered length 107 of outer tube 101 to cover remaining length of outer tube 101 using an outer tube cover sheath 120. Tube cover has a distal edge configured to resist penetration of outer tube 101 into soft tissue beyond the uncovered length. Outer tube 101 includes measurement readings 108 arranged to facilitate visual reading of a dimension indicative of uncovered length 107 (FIG. 8B); such readings can assist in pre-penetration preparations or be visualized from within the body, such as by a laparoscope present at a different laparoscopic entry or by an imaging equipment.

Figure 13A:
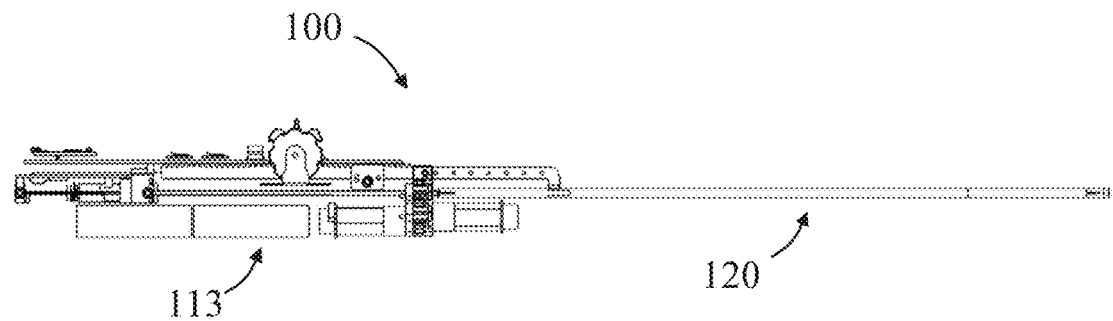
FIGS. 13A-13D illustrate views of the apparatus shown in FIG. 7A representing several exemplary scenarios of operation thereof, according to some embodiments.
Figure 13B:
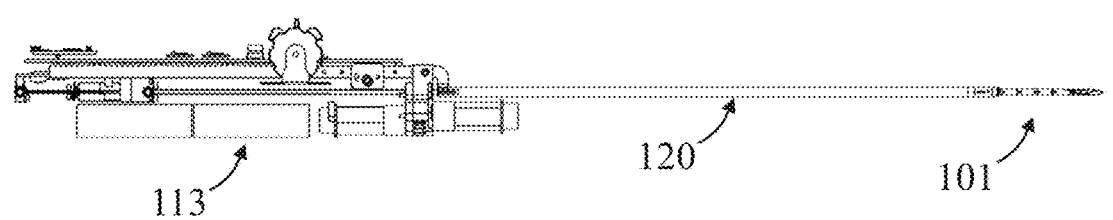

First control 114 is operatively connected to outer tube cover sheath 120 using an uncovering mechanism rack and pinion actuator 121 connected to a push rod 122 (for transmitting knob rotation motions to push rod linear motions). The knob constructed control 114 is finger-operated by forward or backward rotation to force corresponding linear motion of push rod 122 that is fixedly connected to cover sheath 120 and transmits thereto the motions applied via first control 114. Cover sheath 120 is slidable over outer tube 101 between a proximal-most position (shown in FIG. 13A), in which outer tube tip 102 is covered within cover sheath 120, and a distal-most position in which cover sheath 120 is maximally withdrawn to uncover a predetermined maximal uncovered length of outer tube 101 (as shown in FIG. 13B, for example).

FIGS. 11A-11B illustrate respectively a full side view and a zoom-in partial side view of inner needle 105 in an unstressed relaxed state (in which no external forces or internal stresses are applied in a manner sufficient to deform its size and/or shape, at least not significantly and/or visually). Inner needle 105 is configured such that when its protruding portion progresses through the soft tissue, tissue infiltration into its lumen is minimized or even prevented, and its protruded portion effectively resists straightening from its unstressed, relaxed shape. Inner needle body 123 in its unstressed relaxed state includes a flexible curved segment 124 with a radius of curvature within a range of 15 mm to 45 mm. Curved segment 124 optionally provides the maximally allowed length for protruding portion 109. When in the unstressed relaxed state, curved segment 124 forms an arc subtending an angle $\gamma_{max}$ of at least 225°, optionally at least 270°, and is configured with elastic resistance to straightening within a range of 2 N to 20 N. When straighten, length of curved segment 124 is optionally at least 40 mm, optionally at least 100 mm, or optionally at least 250 mm.

Figure 13C:
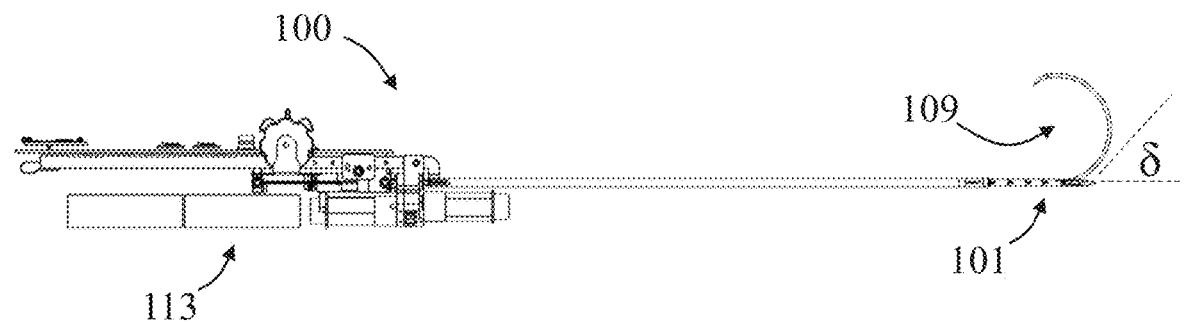

A distal segment 125, which ends with needle tip 106, adjoins curved segment 124 with a bending 129 (optionally an inward bending, inclined towards center of curvature of curved segment 124) having a bending angle θ within a range of 5° to 25° relative to a tangent projection to curved segment 124 at bending 129. Distal segment 125 includes an outer curved side 148 and an inner straight side 149, adjoining with the sharp needle tip 106. Inner straight side 149 encloses the inner needle opening, such that the opening is positioned laterally to needle tip 106, and inwardly (at least partially towards center of curved segment 124), when inner needle 105 is pushed through soft tissue via outer tube 101. Inner needle 105, with distal segment 125 thereof, is configured such that protruding portion 109 of inner needle 105 exits outer tube opening 104 with a needle exit angle δ within a range of 10° to 80°, optionally within a range of 20° to 50°, relative to outer tube 101 (as shown in FIG. 13C). A proximal segment 126 adjoined curved segment 124, optionally straight along its length, provided with threads 127 (shown in FIG. 9B) that are configured to function as a rack member in a needle rack and pinion actuator 128.

Figure 9B:
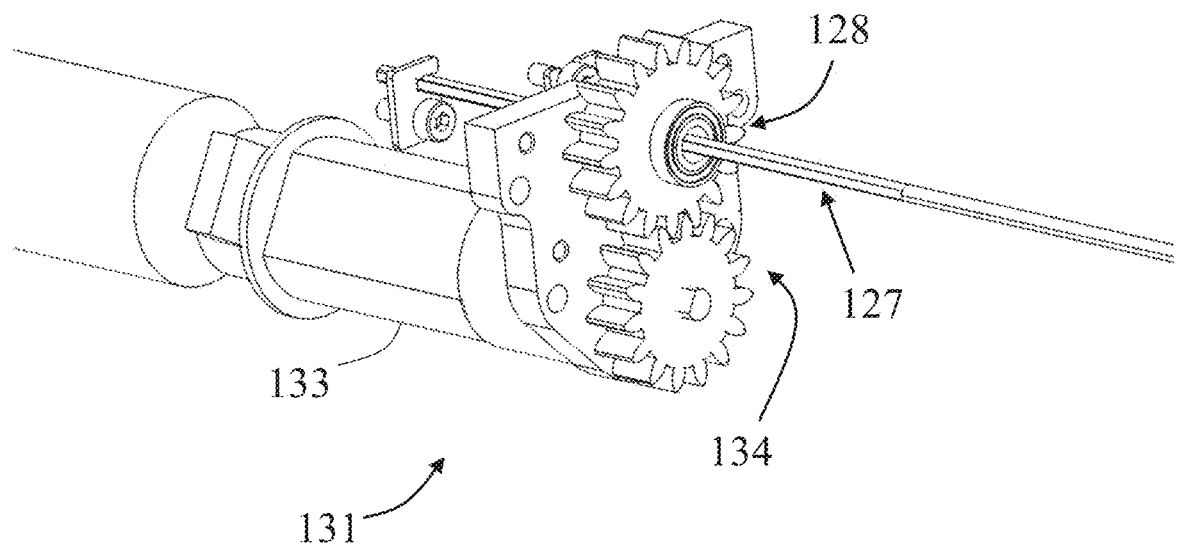

FIGS. 9A-9B illustrate respectively a full isometric view and a zoom-in partial isometric view of inner needle advancing mechanism 117 provided in apparatus 100. Inner needle advancing mechanism 117 is powered by one or more batteries 129 and includes an inner needle protrusion controller 130 configured to operatively control advancement of inner needle 105 within outer tube 101. Inner needle protrusion controller 130 is operateable using second control 116 and includes an inner needle motion generator 131 and a needle printed circuit board 132. Second control 116 is operatively connected to inner needle motion generator 131 to selectively force axial movement of the inner needle within the outer tube and includes a needle motor 133 and a needle gear mechanism 134. By switching second control 116 in a certain direction, inner needle protrusion controller 130 comes into play and the programmed PCB 132 orders batteries 129 to power needle motor 133 in a corresponding direction. Via needle gear mechanism 134, the rotary motion is transferred to needle rack and pinion actuator 128 and transited to linear motion for shifting inner needle 105 forward or backward. Needle motion generator 131 is configured to force by default axial movement of tension member passer 110 with inner needle 105 such that both advance and withdraw together within outer tube 101. FIG. 13B shows apparatus 100 when inner needle 105 is fully retracted within outer tube 101, and FIG. 13C shows apparatus 100 when a protruding portion 109 of inner needle 105 protrudes in a curved form via outer tube opening 104.

FIG. 12 illustrates a side view of tension member passer 110 in an unstressed relaxed state (in which no external forces or internal stresses are applied in a manner sufficient to deform its size and/or shape, at least not significantly and/or visually), with its main components—tension member passer body 111 and tension member passer securing member 112—configured in a snare like form. Tension member passer body 111 is flexible and elastic and preferably solid (with no lumen extending along part or all its length).

Tension member passer 110 is configured to exit the inner needle lumen in a straight form, and optionally tangent thereto, and to keep straight when it is further advanced until a curved or bending point provided along its length reaches the inner needle opening, allowing it to incline relative to inner needle 105. Tension member passer body 111 has a curved or bent portion 135 forming a deviated tension member passer distal end portion 136, which is substantially straight and extends along a length DL which is optionally at least 10 mm, or optionally particularly between about 15 mm and about 30 mm. If, prior to tension member passer protrusion, inner needle tip 106 is distanced less than length DL from outer surface of the treated internal body region (e.g., outer surface OS), then tension member passer 110 will advance in a straight path until reaching or crossing the outer surface of the treated body region. Contrarily, if needle tip 106 is distanced substantially more than length DL, then tension member passer 110 will begin its progress in a straight form but eventually will curve and continue its advancing in a curved path. The deviated tension member passer distal end portion 136 forms with remainder of tension member passer body 111 a deviation angle ε within a range of 15° to 55°, optionally about 35°. Curved or bent portion 135 is configured with elastic resistance to straightening within a range of 0.1 N to 1 N.

Tension member passer securing member 112 includes a securing wire portion 137 extending from a first location 138 at distal end portion 136 to a second location 139 on the tension member passer body 111 proximally to curved or bent portion 135. Securing wire portion 137 is similar in length to length of a segment of tension member passer body 111 extending from first location 138 to second location 139, and form together a symmetric, elastic, normally-opened, loop 147, optionally shaped in a 'diamond', 'oval' or 'vesica piscis' (pointed oval) contour. Optionally, loop 147 is sized to allow passing therethrough of a grasper holding a suture, optionally having a width within a range of 2 mm to 10 mm, optionally about 5 mm. When deviated tension member passer distal end portion 136 is forced to align with rest of tension member passer body 111, securing wire portion 137 is configured to undergo increased tension, so that loop 147 compresses and can therefore hold a tension member (e.g., suture) passing therethrough. When tension member passer securing member 112 extends fully within a space of sufficient size, such as within abdominal cavity AC, loop 147 can elastically (voluntarily) expand to an open form. Optionally, securing member 112 is formed of a super elastic material, optionally Ni—Ti alloy, and/or optionally of same material as tension member passer body 111 yet in smaller width and/or different thermal conditioning. Tension member passer 110 ends with a sharp tension member passer tip 140 configured to cut through soft tissue when pressed therethrough in sufficient force.

Figure 10B:
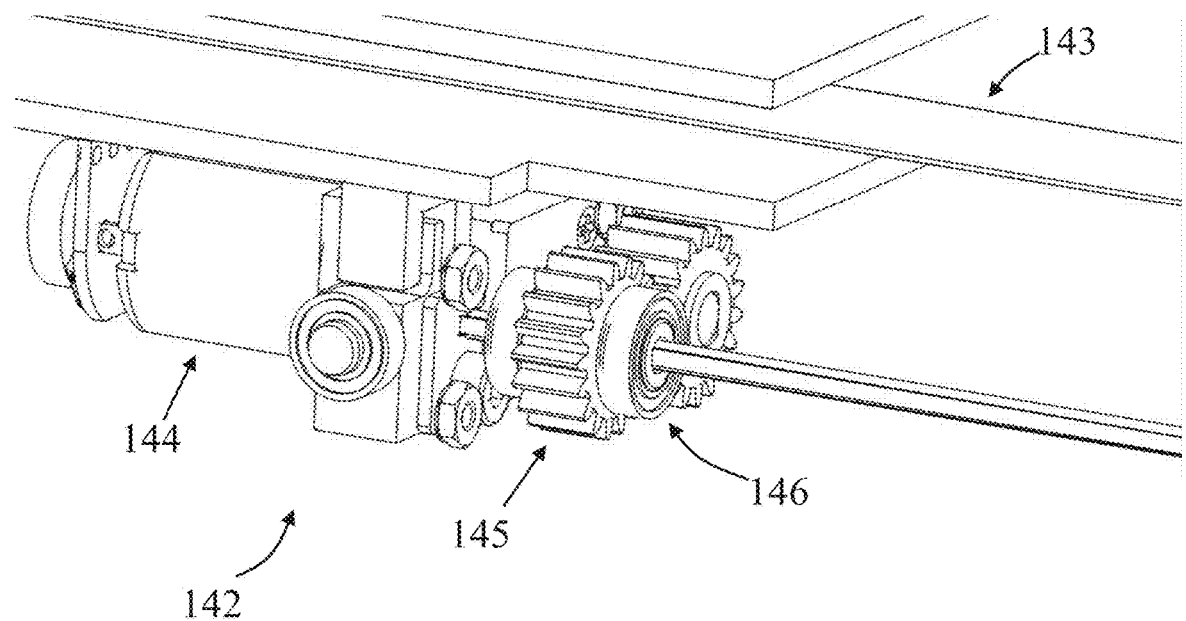
Figure 13D:
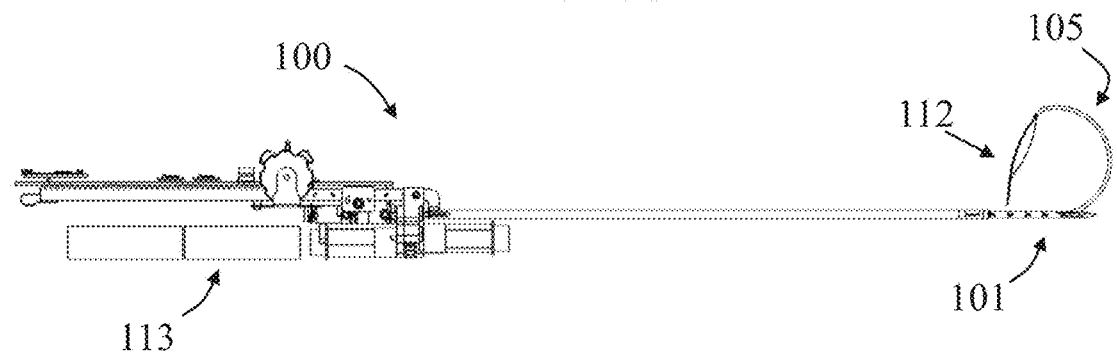

FIGS. 10A-10B illustrate respectively a full isometric view and a zoom-in partial isometric view of tension member passer advancing mechanism 119 provided in apparatus 100. Tension member passer advancing mechanism 119 is also powered by batteries 129 and includes a tension member passer protrusion controller 141 configured to operatively control advancement of tension member passer body 111 within inner needle 105. Tension member passer protrusion controller 141 is operable using third control 118 and includes a tension member passer motion generator 142 and a tension member passer printed circuit board 143. Third control 118 is operatively connected to tension member passer motion generator 142 to selectively force axial movement of tension member passer 110 within inner needle 105. Tension member passer motion generator 142 includes a tension member passer motor 144 and a tension member passer gear mechanism 145. By switching third control 118 in a certain direction, tension member passer protrusion controller 141 comes into play and the programmed tension member passer PCB 143 orders batteries 129 to power tension member passer motor 144 in a corresponding direction. Via tension member passer gear mechanism 145, the rotary motion is transferred to a tension member passer rack and pinion actuator 146 and translates to linear motion for shifting tension member passer 110 forward or backward relative to inner needle 105. Tension member passer PCB 143 can be configured such that tension member passer protrusion controller 141 can be activated to advance tension member passer body 111 only after needle protrusion controller 130 finishes advancing of inner needle 105 up to a user defined length of protruding portion 109. FIG. 13C shows apparatus 100 when tension member passer 110 is fully retracted within inner needle 105, and FIG. 13D shows apparatus 100 when tension member passer securing member 112 protrudes from inner needle 105.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosure.

Throughout this disclosure, a numerical value of a parameter, feature, characteristic, object, or dimension, may be stated or described in terms of a numerical range format. Such a numerical range format, as used herein, illustrates implementation of some exemplary embodiments, and does not inflexibly limit the scope of the exemplary embodiments. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', and is considered equivalent to, and meaning the same as, the phrase 'room temperature refers to a temperature in a range of from about 20° C. to about 25° C.'.

The term 'about', as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

What is claimed is:

1. An apparatus for passing a tension member around volumetric region of an organ, the apparatus comprising:
    a rigid outer tube comprising a sharp outer tube tip and an outer tube lumen with an outer tube opening in proximity to the outer tube tip;
    an inner needle comprising an elastic needle body curved at least in part thereof, the inner needle ending with a sharp needle tip and enclosing an inner needle lumen with an inner needle opening being in proximity to the needle tip, the inner needle body being configured to pass straightened through the outer tube lumen and to partially protrude via the outer tube opening, such that a protruding portion of the inner needle body is allowed to voluntarily flex to a curved form having diameter equal to or greater than diameter of the volumetric region; and
    a tension member passer comprising a tension member passer body, sized for passing through the inner needle lumen, and a tension member pulling portion configured for engaging with a portion of the tension member and for continuously applying a pulling force to the engaged portion of the tension member when the tension member is withdrawn with the tension member passer;
    wherein the tension member passer body has a curved or bent portion forming a deviated distal end portion inclined relative to remainder of the tension member passer body;
    wherein the tension member pulling portion includes a securing wire portion extending from a first location on the tension member passer body, distally to the curved or bent portion, to a second location on the tension member passer body, proximally to the curved or bent portion;
    wherein the securing wire portion is configured to undergo increased tension when the deviated tension member passer body distal end portion is forced to align with rest of the tension member passer body, and/or the deviated tension member passer body distal end portion originates at the first location and extends in a straight form at least 10 mm in length;
    wherein the apparatus is configured for forming a passage through the organ, the passage extending along a plane crossing the volumetric region from an entry point at a surface of the organ, located in front of a first side of the volumetric region, to an exit point at the surface of the organ, located in front of a second side of the volumetric portion opposite to the first side, and the apparatus is further configured for passing the tension member around the volumetric region by pulling the tension member from the exit point to the entry point through the passage.

2. An apparatus according to claim 1, wherein the volumetric region of the organ includes a tissue mass comprising at least a portion of a tumor.

3. An apparatus according to claim 1, wherein the outer tube is movable relative to a covering portion of the apparatus until the outer tube tip extends a chosen uncovered length from a distal edge of the covering portion, the distal edge is configured to resist penetration into soft tissue to inhibit insertion of the outer tube to a depth greater than the uncovered length.

4. An apparatus according to claim 1, wherein the elastic needle body is configured with elastic resistance to straightening within a range of 2 N to 20 N.

5. An apparatus according to claim 1, configured such that the protruding portion exits the outer tube opening with a needle exit angle δ within a range of 10° to 80°, relative to the outer tube.

6. An apparatus according to claim 1, wherein the tension member passer body is flexible and elastic.

7. An apparatus according to claim 1, wherein the tension member pulling portion includes a securing member forming a loop with the tension member passer body.

8. An apparatus according to claim 1, wherein the deviated tension member passer body distal end portion forms with rest of the tension member passer body a deviation angle within a range of 15° to 55°.

9. An apparatus according to claim 1, wherein the curved or bent portion of the tension member passer body is configured with elastic resistance to straightening within a range of 0.1 N to 1 N.

10. An apparatus according to claim 1, wherein the securing wire portion is similar in length to length of a segment of the tension member passer body extending from the first location to the second location.

11. An apparatus according to claim 1, further comprising a console.

12. A method for passing a tension member around a volumetric region of an organ, the method comprising:
   using a rigid outer tube, comprising a sharp outer tube tip and an outer tube lumen with an outer tube opening in proximity to the outer tube tip, penetrating through an entry point into the organ such that the outer tube tip reaches a penetration depth;
   passing an inner needle in the outer tube lumen, the inner needle includes an elastic needle body curved at least in part thereof, ending with a sharp needle tip and enclosing an inner needle lumen with an inner needle opening in proximity to the needle tip;
   piercing a curved passage with the needle tip around the volumetric region with a protrusion length of a protruding portion of the inner needle body, by pushing the inner needle via the outer tube opening and allowing the protruding portion to voluntarily flex to a curved form having diameter equal to or greater than diameter of the volumetric region;
   advancing a tension member passer comprising a tension member passer body and a tension member pulling portion, in the inner needle lumen and via the inner needle opening, until the tension member pulling portion exits the organ at an exit point opposing the entry point relative to the volumetric region; and
   drawing the tension member into and through the curved passage by pulling the tension member passer with the tension member.

13. A method according to claim 12, wherein the drawing includes extending the tension member around the volumetric region such that one end of the tension member projects from the entry point and another end of the tension member projects from the exit point.

14. A method according to claim 13, wherein the organ is an internal organ located within a body of a live subject, and the method further comprising forming a surgical route from outside the body of the subject and delivering the outer tube through the surgical route until the outer tube tip reaches the organ.

15. A method according to claim 14, wherein the organ is a uterus.

16. A method according to claim 12, wherein the volumetric region of the organ includes a tissue mass comprising at least a portion of a tumor.

17. A method according to claim 12, comprising ending the piercing with positioning the needle tip at a chosen distance from a surface of the organ, so as to form a needle tip angle between the needle tip and the surface of the organ.

18. A method according to claim 17, wherein the distance is smaller than 3 cm, and/or the needle tip angle is within a range of 10° to 60°.

19. A method according to claim 12, further comprising defining a penetration angle between the outer tube and a perpendicular line to a surface of the organ at the entry point, wherein the protrusion length subtends a subtended angle is at least 270° minus the penetration angle.

20. A method according to claim 12, wherein the penetrating, the passing, the piercing, and/or the advancing is repeated, each repetition is performed using a different implanted tension member, a different entry point and a different exit point.

21. A method according to claim 12, wherein both the entry point and the exit point are formed at opposing sides of the volumetric region along a surface of the organ.

22. A method according to claim 12, wherein the entry point and the exit point are formed on a surface of the organ at a chosen distance therebetween.

23. A method according to claim 22, wherein the chosen distance between the entry point and the exit point on the surface of the organ is 5 cm or less.

24. A method according to claim 12, further comprising:
   visualizing a surface of the organ using an endoscope or a camera positioned in an abdominal cavity of the subject; and
   keeping the entry point and the exit point within visual range via the endoscope or the camera.

* * * * *